US012773390B2

(12) United States Patent
Hematti et al.

(10) Patent No.: US 12,773,390 B2
(45) Date of Patent: Oct. 27, 2026

(54) COMPOSITIONS AND METHODS FOR TREATING CANCER

(71) Applicant: Wisconsin Alumni Research Foundation, Madison, WI (US)

(72) Inventors: Peiman Hematti, Madison, WI (US); Hau Le, Madison, WI (US); Bindu Nair, Madison, WI (US); John Kink, Madison, WI (US); J. Leon Shohet, Madison, WI (US); Manh Ha Nguyen, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 62 days.

(21) Appl. No.: 18/828,865

(22) Filed: Sep. 9, 2024

(65) Prior Publication Data

US 2025/0099391 A1 Mar. 27, 2025

Related U.S. Application Data

(60) Provisional application No. 63/581,484, filed on Sep. 8, 2023.

(51) Int. Cl.

| | |
|---|---|
| ***A61K 9/50*** | (2006.01) |
| ***A61K 35/13*** | (2015.01) |
| ***A61K 39/395*** | (2006.01) |
| ***A61K 47/42*** | (2017.01) |
| ***A61K 47/68*** | (2017.01) |
| ***A61K 47/69*** | (2017.01) |
| ***A61P 35/00*** | (2006.01) |
| ***H05H 1/26*** | (2006.01) |

(52) U.S. Cl.

CPC .......... *A61K 9/5068* (2013.01); *A61K 9/5089* (2013.01); *A61K 35/13* (2013.01); *A61K 39/3955* (2013.01); *A61K 47/42* (2013.01); *A61K 47/6851* (2017.08); *A61K 47/6913* (2017.08); *A61P 35/00* (2018.01); *H05H 1/26* (2013.01); *H05H 2240/10* (2013.01); *H05H 2245/30* (2021.05)

(58) Field of Classification Search

CPC ............. A61K 9/5068; A61K 47/6907; A61K 47/6909; A61K 47/6911; A61K 47/6913; A61K 47/6915; A61K 47/6917; A61K 9/5089; A61K 35/13; A61P 35/00; H05H 2245/30

See application file for complete search history.

(56) References Cited

U.S. PATENT DOCUMENTS

| | | | | |
|---|---|---|---|---|
| 2021/0085724 | A1* | 3/2021 | Marban | A61K 35/34 |
| 2021/0093567 | A1 | 4/2021 | Lee et al. | |
| 2023/0277458 | A1* | 9/2023 | Canady | A61K 9/1277 424/450 |
| 2023/0313147 | A1 | 10/2023 | Canady et al. | |

FOREIGN PATENT DOCUMENTS

| | | | |
|---|---|---|---|
| JP | 2022-543851 | A | 10/2022 |
| WO | 2018/035204 | A1 | 2/2018 |

OTHER PUBLICATIONS

International Search Report and Written Opinion issued in Int'l Application No. PCT/US2024045839, mailed Jan. 23, 2025, 28 pages.

Resnik, M. et al., "Extracellular Vesicle Isolation Yields Increased by Low-Temperature Gaseous Plasma Treatment of Polypropylene Tubes", Polymers, 2020, 12(10), p. 2363.

Yan, D. et al., "Cold atmospheric plasma, a novel promising anti-cancer treatment modality", Oncotarget, 2017, 8(9), 15977-15995.

Reuter, S. et al., "From RONS to ROS: Tailoring Plasma Jet Treatment of Skin Cells", IEEE Transaction on Plasma Science, 2012, 40(11), 2986-2993.

Kolb, J. F. et al., "Cold atmospheric pressure air plasma jet for medical applications", Applied Physics Letters, 2008, 92(24), p. 241501.

Bang, C. et al. "Exosomes: New players in cell-cell communication", The International Journal of Biochemistry & Cell Biology, 2012, 44(11), 2060-2064.

* cited by examiner

*Primary Examiner* — Michael B. Pallay

(74) *Attorney, Agent, or Firm* — McDonnell Boehnen Hulbert & Berghoff LLP

(57) ABSTRACT

The disclosure relates to compositions and methods for treating cancer using cold atmospheric plasma-modified extracellular vesicles generated using a CAP jet device.

18 Claims, 14 Drawing Sheets

Glass Bottle Reactor

UV-transmitting Cuvette Reactor 4-well Cell-Culture Plate Reactor

COMPOSITIONS AND METHODS FOR TREATING CANCER

CROSS-REFERENCE TO RELATED APPLICATION

This application claims priority to U.S. Provisional Application No. 63/581,484, filed Sep. 8, 2023, which is incorporated by reference in its entirety.

STATEMENT REGARDING FEDERALLY SPONSORED RESEARCH

This invention was made with government support HL153721 awarded by the National Institutes of Health and under 2019-67017-29179 awarded by the USDA/NIFA. The government has certain rights in the invention.

BACKGROUND OF THE DISCLOSURE

Field of Invention

This disclosure relates to compositions and methods to treat cancer using a CAP jet device.

Technical Background

Glioblastoma (GBM) is one of the most deadly and recalcitrant solid cancers, with an overall 5-year survival rate of 10%. The current treatment for GBM includes maximal safe resection, followed by radiation therapy and concomitant chemotherapy with temozolomide (TMZ), and finally, with adjuvant TMZ. Despite recent medical advances, most GBM patients experience recurrence by 8 months.

Cold atmospheric plasma (CAP) is produced at atmospheric pressure when a carrier gas is ionized as it moves between two electrodes with a high-voltage applied between them, enabling its use in biomedicine. CAP contains dozens of reactive oxygen and nitrogen species (RONS). Compared to normal, healthy cells, cancer cells are particularly sensitive to RONS; hence, harnessing CAP-generated RONS for cancer therapy is an attractive prospect. However, a major obstacle in applying CAP in clinical settings is the limit in the depth of tissue penetration by CAP when it is applied directly.

In the context of GBM, a cancer that occurs in the brain, or other internally located cancers, there are no available options for directly introducing the therapeutic benefits that CAP might provide. And, it is not clear whether CAP could safely be introduced into the brain or systemically without harmful side effects. Therefore, a critical need exists for further development of new treatment methods and compositions for treating GBM and other cancers that can safely harness and effectively apply the therapeutic benefit of CAP.

BRIEF SUMMARY

In a first aspect, the present disclosure provides a method for generating CAP-modified extracellular vesicles (EVs) for the treatment of cancer, the method comprising the steps of:

(a) obtaining a sample of cancer cells or tissues of cancer cell origin;

(b) isolating EVs from the sample;

(c) preparing a cold atmospheric plasma (CAP); and (d) exposing the EVs to the CAP to modify the EVs with CAP-derived reactive oxygen and nitrogen species.

In one embodiment of the first aspect, the EVs comprise exosomes (30-200 nm), microvesicles (50-1000 nm), and/or apoptotic bodies (500-2000 nm).

In one embodiment of the first aspect, the sample is a biopsy, a fluid, a perfusate of an organ, media collected from a homogenate of an organ, cultured cells, a cultured tissue, or a cultured organ.

In one embodiment of the first aspect, the sample is cultured cells, a cultured tissue, or a cultured organ.

In one embodiment of the first aspect, the sample is cultured in EV-free media.

In one embodiment of the first aspect, the modified EVs comprise long half-life RONS.

In one embodiment of the first aspect, the sample is frozen. In one embodiment, the sample is thawed before being exposed to CAP. In one embodiment, the sample is exposed to CAP before EVs are isolated.

In one embodiment of the first aspect, the cancer cells are derived from glioblastoma, neuroblastoma, Wilms' tumor, breast cancer, colorectal cancer, lung cancer, liver cancer, kidney cancer, appendiceal cancer, desmoplastic small cell cancer, mesothelioma, ovarian cancer, peritoneal cancer, gastric cancer, malignant ascites, bladder cancer, blood cancer, bone cancer, soft tissue cancer, skin cancer, or pancreatic cancer.

In one embodiment of the first aspect, the tissue of cancer-cell origin comprises central-nervous system (CNS)-associated tissue, skin tissue, liver tissue, bone tissue, soft tissue, kidney tissue, breast tissue, colonic tissue, pleural fluid, peritoneal fluid, urine, serum, lung tissue, or pancreatic tissue.

In one embodiment of the first aspect, the tissue of cancer-cell origin is obtained from an individual to be treated.

In one embodiment of the first aspect, the tissue of cancer-cell origin is allogeneic or xenogeneic.

In one embodiment of the first aspect, the tissue of cancer-cell origin is differentiated from an embryonic or induced pluripotent stem cell.

In one embodiment of the first aspect, the central-nervous system (CNS)-associated tissue comprises cerebrospinal fluid.

In one embodiment of the first aspect, the EVs are isolated from the sample by ultracentrifugation, ultrafiltration, size-exclusion chromatography, precipitation, immunoaffinity capture, and/or a microfluidics-based isolation.

In one embodiment of the first aspect, the CAP is prepared from helium, argon, nitrogen, heliox, water vapor, and/or air.

In one embodiment of the first aspect, the CAP is prepared from helium.

In one embodiment of the first aspect, the EVs are exposed to the CAP for about 1 minute to about 30 minutes.

In a second aspect, the present disclosure provides a method for generating CAP-modified EVs for the treatment of a cancer, the method comprising the steps of:

(a) differentiating a cell or a tissue from an embryonic or induced pluripotent stem cell, wherein the cell or tissue is differentiated into a cell or tissue of cancer origin;

(b) isolating EVs from the differentiated cell or tissue;

(c) preparing a cold atmospheric plasma (CAP); and (d) exposing the EVs to the CAP to modify the EVs with CAP-derived reactive oxygen and nitrogen species.

In one embodiment of the second aspect, the cell is a mesenchymal stromal cell, an astrocyte, a monocyte, a macrophage, a dendritic cell, a T cell, a B-cell, a fibroblast, or a stem cell.

In a third aspect, the present disclosure provides a pharmaceutical composition for treating cancer, comprising:

(a) a therapeutically effective amount of CAP-modified EVs according to any one of the first or second aspects and embodiments thereof; and (b) at least one pharmaceutically acceptable carrier, solvent, adjuvant, or diluent.

In one embodiment of the third aspect, the least one pharmaceutically acceptable carrier, solvent, adjuvant, or diluent comprises a phosphate-buffered saline, a normal saline, a Ringers solution, a plasmolyte solution, and/or an albumin solution.

In one embodiment of the third aspect, the pharmaceutical composition further comprises an additive.

In one embodiment of the third aspect, the additive comprises trehalose and/or a protein carrier.

In one embodiment of the third aspect, the protein carrier comprises albumin.

In one embodiment of the third aspect, the CAP-modified EVs further comprise a tumor specific antibody attached to a surface.

In one embodiment of the third aspect, the composition is lyophilized.

In one embodiment of the third aspect, the pharmaceutical composition further comprises a secondary therapeutic agent.

In one embodiment of the third aspect, the secondary therapeutic agent comprises a chemotherapeutic compound and/or a checkpoint inhibitor antibody.

In one embodiment of the third aspect, the therapeutically effective amount of CAP-modified EVs comprises about $1\times10^{11}$ to about $1\times10^{14}$ EVs.

In a fourth aspect, the present disclosure provides a method of treating cancer in a subject in need thereof, comprising:

(a) obtaining a sample from a cancerous tumor or a tissue of cancerous tumor origin;

(b) isolating EVs from the sample;

(c) preparing a cold atmospheric plasma (CAP);

(d) exposing the EVs to the CAP to modify the EVs with CAP-derived reactive oxygen and nitrogen species; and (e) administering a therapeutically effective amount of the CAP-modified EVs to the subject, wherein administration of the CAP-modified EVs kills tumor cells, suppresses tumor-cell growth, and/or slows tumor-cell growth.

In one embodiment of the fourth aspect, the sample is obtained from the subject.

In one embodiment of the fourth aspect, the sample is obtained from another individual having the same type of cancer as the subject.

In one embodiment of the fourth aspect, non-cancerous cells are not adversely affected by the CAP-modified EVs.

In a fifth aspect, the present disclosure provides a method of treating glioblastoma (GBM) in a subject in need thereof, comprising:

(a) obtaining a sample from cerebrospinal fluid of the subject;

(b) isolating EVs from the sample;

(c) preparing a cold atmospheric plasma (CAP);

(d) exposing the EVs to the CAP to modify the EVs with CAP-derived reactive oxygen and nitrogen species; and (e) administering a therapeutically effective amount of the CAP-modified EVs to the subject, wherein the CAP-modified EVs kill GBM cells in the subject without significantly affecting normal astrocytes.

In some embodiments, a therapeutically effective amount of CAP-modified EVs comprises about $1\times10^{11}$ to about $1\times10^{14}$ EVs.

In some embodiments, a therapeutically effective amount of CAP-modified EVs is administered to a subject in a dose of about $2\times10^{10}$ to about $1\times10^{14}$/kg.

In a sixth aspect, the present disclosure provides a cold atmospheric plasma (CAP) jet for application of plasma-cancer treatment, comprising:

(a) a dielectric tube having a length of about 50 mm to about 250 mm, an outer diameter in range of about 1 mm to about 10 mm, and an inner diameter of about 0.01 mm to about 5 mm, wherein the inner diameter defines an interior of the dielectric tube, and wherein the interior of the dielectric tube is configured to receive a stream of a feed gas or a gas mixture via:

(i) a gas tank, wherein the gas tank supplies the feed gas, (ii) a gas-tubing system, wherein the feed gas is configured to flow from the gas tank through the gas-tubing system into the dielectric tube, (iii) a gas regulator, wherein the gas regulator regulates the feed gas before it is fed into the dielectric tube, and (iv) a flow meter, wherein the flow meter is positioned between the gas tank and the gas tubing system, and wherein the flow meter controls the flow rate of the feed gas through the gas tubing system;

(b) a high-voltage power supply;

(c) an internal pin or wire electrode that at least partially extends into the interior of the dielectric tube, wherein the internal electrode is electrically connected to an output of the high-voltage power supply; and (d) an external coil or wire electrode that wraps around a lower portion of the outer diameter of the dielectric tube connected to the grounded output of the high-voltage power supply.

In one embodiment of the sixth aspect, the external electrode is mounted on the dielectric tube by use of a gasket.

In one embodiment of the sixth aspect, the gasket is an O-ring gasket.

In one embodiment of the sixth aspect, the external electrode is grounded through a resistor to limit the current in to approximately less than 10 mA so that arcing is prevented.

In one embodiment of the sixth aspect, the internal electrode and the external electrode are each electrically insulated.

In a seventh aspect, the present disclosure provides a cold atmospheric plasma (CAP) jet, comprising:

(a) a dielectric tube having a length of about 160 mm long and an outer diameter of about 4.2 mm and an inner diameter of about 2.4 mm, wherein the inner diameter defines an interior of the dielectric tube, and wherein the interior of the dielectric tube is configured to receive a stream of feed gas (e.g., helium gas);

(b) a high-voltage power supply, wherein the high-voltage power supply comprises a signal generator and a high-voltage amplifier;

(c) an internal electrode that extends into the interior of the dielectric tube by about 145 mm from a top of the dielectric tube, wherein the internal electrode is electrically connected to an output of the high-voltage power supply; and (d) an external coil or wire electrode that wraps around a portion of the outer diameter of about 5 mm in length of the dielectric tube that begins about 5 mm lower than an inserted end of the internal electrode, wherein the external electrode is mounted on the dielectric tube by use of an O-ring gasket, and wherein the external electrode is grounded through a resistor, wherein the internal electrode and the external electrode are each electrically insulated by a coating of an electrically insulating material.

In an eighth aspect, the present disclosure provides a cold atmospheric plasma jet, comprising:

(a) a dielectric tube having a length of about 160 mm and an outer diameter of about 4.2 mm and an inner diameter of about 2.4 mm, wherein the inner diameter defines an interior of the dielectric tube, and wherein the interior of the dielectric tube is configured to receive a stream of helium or other gas;

(b) a high-voltage power supply, comprising:

(i) a computer, wherein a program running on a computer is used to communicate with other components of the high-voltage power supply and to control the jet device operation, (ii) a signal generator connected to the computer via a high-speed USB-adapted cable, wherein the signal generator is a pulse/function generator that receives one or more commands from the program on the computer such that the one or more commands define a series of output signals having various function waveforms, and wherein the signal generator is configured to generate the series of output signals based on the one or more commands, and (iii) a high-voltage amplifier configured to receive the series of output signals from the signal generator and amplify each output signal of the series of output signals to the high voltages that can break down the feed gas to make dielectric discharges;

(c) an internal pin or wire electrode that extends into the interior of the dielectric tube by about 145 mm from a top of the dielectric tube, wherein the internal electrode is electrically connected to an output of the high-voltage power supply; and (d) an external coil or electrode that wraps around a portion of the outer diameter of about 5 mm in length of the dielectric tube that begins about 5 mm lower than an inserted end of the internal pin electrode, wherein the external coil electrode is mounted onto the dielectric tube by use of an O-ring gasket, and wherein the external-coil electrode with it two ends are grounded via connecting together at one end of a 100 MΩ resistor while the other end of the resistor is connected to the ground of the high voltage power supply, wherein the internal electrode and the external electrode are each electrically insulated by a film of coating made of an electrical-insulating material.

In a ninth aspect, the present disclosure provides a method of using a cold atmospheric plasma jet, comprising:

(a) generating, at a program on a computer, one or more commands, wherein the one or more commands define a series of output signals, and wherein the series of output signals form one or more waveform patterns;

(b) sending, by the computer, the one or more commands to a signal generator for the high-voltage power supply of the cold atmospheric plasma jet, wherein the cold atmospheric plasma jet comprises:

a dielectric tube having an outer diameter and an inner diameter, wherein the inner diameter defines an interior of the dielectric tube, and wherein the interior of the dielectric tube is configured to receive a stream of a feeding gas;

an internal pin or wire electrode that at least partially extends into the interior of the dielectric tube, wherein the internal electrode is electrically connected to output of the high-voltage power supply; and an external coil or wire electrode that wraps around a lower portion of the outer diameter of the dielectric tube, wherein the external electrode is coupled to the dielectric tube by using an O-ring gasket, and wherein the external electrode is grounded through a resistor, wherein the internal electrode and the external electrode are each electrically insulated;

(c) generating, at the signal generator of the high-voltage power supply, the series of output signals based on the one or more commands;

(d) sending, from the signal generator of the high-voltage power supply to a high-voltage amplifier of the high-voltage power supply, the series of output signals;

(e) amplifying, at the high-voltage amplifier of the high-voltage power supply, the magnitude of each output signal of the series of output signals;

(f) outputting, from an output of the high-voltage power supply, the amplified series of output signals;

(g) receiving, at the internal electrode, the amplified series of output signals from the output of the high-voltage power supply;

(h) igniting, between the internal pin electrode and the external coil electrode, an electric discharge;

(i) delivering, by the feed gas or gases out of a nozzle of the dielectric tube, the cold atmospheric plasma jet;

(j) producing hydroxyl or other radicals or molecules that are delivered to treat liquids containing bio-related systems of interest (e.g., exosome, cells, or tissues, etc.);

(k) optimizing the hydroxyl or other radicals or molecules produced by the cold atmospheric plasma jet; and (l) preparing a cold atmospheric plasma treatment of exosome-containing liquids from the optimized production of the hydroxyl radicals.

In some embodiments of the preceding embodiments and aspects, the dielectric tube comprises glass or quartz. In some embodiments of the preceding embodiments and aspects, the electrical-insulating material comprises an aromatic polyimide resin. In some embodiments, the electrical-insulating material has a thickness of about 0.043 mm.

DESCRIPTION OF DRAWINGS

FIG. 9A—Cell viability of normal human astrocytes (NHA) and human glioblastoma cells (SJ-GBM2 and U87) treated with CSF without CAP (CSF, "C"), CAP-treated CSF (CAP CSF; "CC"), CSF without extracellular vesicles and treated with CAP (Ex Free CSF; "C−"), and after adding extracellular vesicles back in to extracellular vesicle-free CSF and treated with CAP (Ex add CSF; C+). CAP CSF (CC) killed the cells in the presence of extracellular vesicles at the same time CAP FBS killed the cells were not exosome dependent. In other words, exosome free samples of CSF even after treating with CAP (C−) could not make a significant cell death but after adding exosomes back (C+) significantly killed the cells (p<0.001). This was not evident in FBS samples. FIG. 9B—Cell viability of normal human astrocytes (NHA) and human glioblastoma cells (SJ-GBM2 and U87) treated with FBS without CAP (FBS; "F"), CAP-treated FBS (CAP FBS; "CF"), FBS without extracellular vesicles and treated with CAP (Ex Free FBS; "F−"), and after adding extracellular vesicles back into extracellular vesicle-free FBS with CAP (Ex add FBS; "F+").

FIGS. 10A & 10B. Extracellular vesicles isolated from the CSF were treated with CAP and added into the cells in an increasing fashion to find out whether more addition of extracellular vesicles could make more cell death. FIGS. 10A and 10B corresponds to two different glioblastoma cells U87 and SJ-GBM2, respectively. *P<0.05; P<0.01; *P<0.001.

Figure 1:
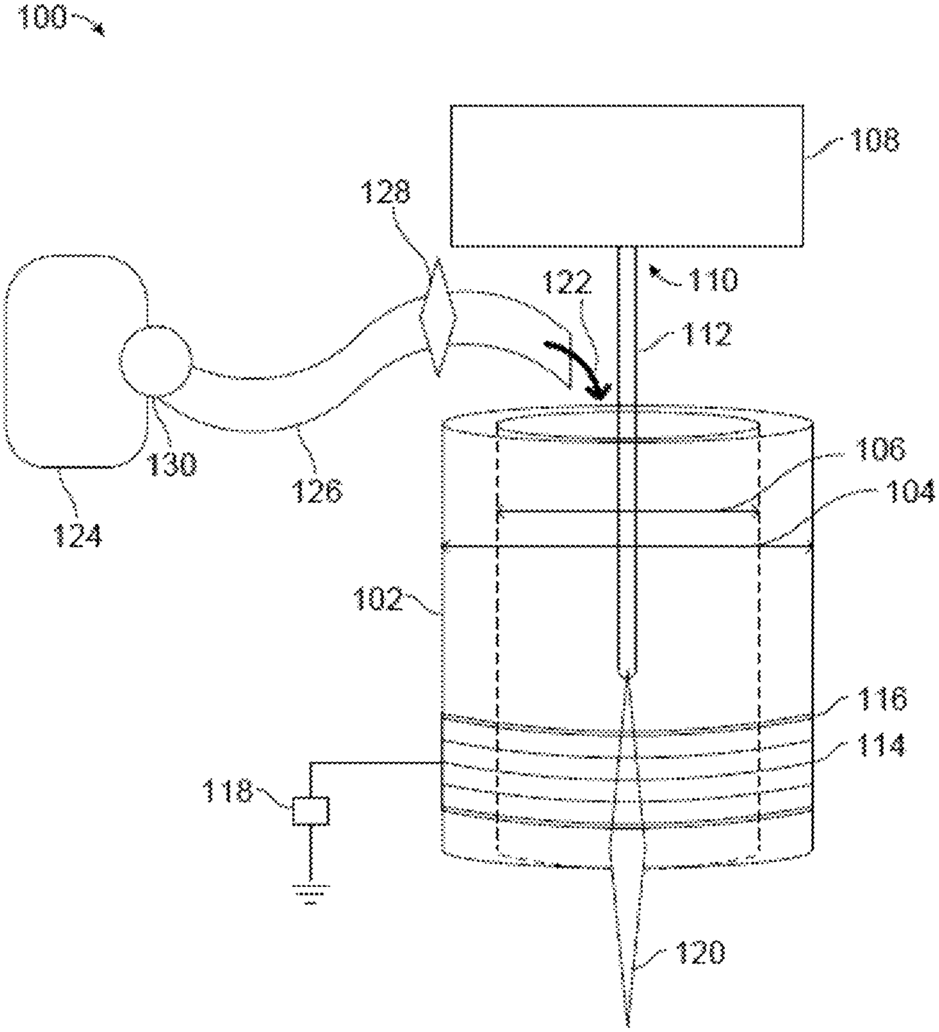
FIG. 1 is a perspective view of a cold atmospheric plasma (CAP) jet for application of plasma-cancer treatment, according to an exemplary embodiment of the present disclosure.

The results demonstrate that extracellular vesicles isolated from CSF (12A) and MSC (12C) can kill glioma cells without harming the normal astrocytes. Moreover, exosomes isolated from cerebrospinal fluid killed significantly more glioma cells, which resulted in a viability of 36% and 46% in SJ-GBM2 and U87, respectively (12A). At the same time, CAP-treated CSF exosomes did not affect normal astrocytes significantly and they were 81.3% alive after 24 hours (12A). Treatment with CAP modified MSC exosomes were also resulted in significant decline in the cell viability of both glioblastoma cells and the astrocytes were unaffected by the treatment (12C). On the other hand, addition of CAP treated exosomes of NHA did not kill any cells significantly, however, one of the cancer cells (SJ-GBM2) treated with NHA exosomes was showing a slight cell proliferation at the end of incubation (12B). Lastly, the CAP modified GBM exosomes showed a significant decrease in all cancer and as well as normal cells (12D). *P<0.05; ***P<0.001.

DETAILED DESCRIPTION

The present disclosure broadly relates to methods for applying the therapeutic benefits of cold atmospheric plasma (CAP) systemically to treat diseases. For example, CAP can be used to produce a composition of activated extracellular vesicles from cerebral spinal fluid (CSF) or other sources for treatment of diseases such as cancer. For example, CAP-modified CSF-derived extracellular vesicles can be used to treat glioblastoma (GBM). In some embodiments, compositions of CAP-modified extracellular vesicles can be used alone for treatment of a disease. In some embodiments, the compositions of CAP-modified extracellular vesicles can be used in combination with one or more additional treatments as described herein elsewhere.

The present disclosure further contains CAP jet devices used to generate CAP as an integral part of the claimed method. However, other devices than these that can generate CAP are not excluded.

In some embodiments, the present disclosure produces and uses CAP-modified extracellular vesicles from CSF to treat GBM effectively. While not wishing to be bound by theory, it is believed that CSF-derived extracellular vesicles have the ability to cross the blood-brain barrier. Therefore, by treating CSF-derived extracellular vesicles with CAP provides CAP-modified extracellular vesicles that can be administered intravenously to reach the brain and treat GBM.

Advantageously, extracellular vesicles have been shown to be safe with little known side effects compared to conventional alternatives like chemotherapy, radiation, or surgery.

In some embodiments, extracellular vesicles from a patient's own CSF or other sources can be treated with CAP and then injected into the CSF of patients with GBM to treat the cancer.

In some embodiments, CAP-modified extracellular vesicles may be useful for treating other cancers. In some instances, the cancer is a primary cancer. In some instances, the cancer is a metastatic cancer. Exemplary cancers include, without limitation, bone cancer, prostate cancer, melanoma (e.g., metastatic melanoma), pancreatic cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia, hairy cell leukemias, acute lymphoblastic leukemias), lymphoma (e.g., non-Hodgkin's lymphomas, Hodgkin's lymphoma), hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer.

In some embodiments, EVs can be sourced from a specific cancer type to be treated, for example, a biopsy from liver cancer can be used to generate CAP-modified EVs to treat liver cancer. In other embodiments, EVs can be sourced from a specific tissue type in which a cancer is found, for example, CSF for brain cancer, blood and/or bone marrow for blood-associated cancer, etc.

In some embodiments, it is envisioned that "off-the-shelf" extracellular vesicles, which can be derived from donors, tissue banks, and/or a patient's own sample, can be treated with CAP just prior to administration. Such "off-the-shelf" extracellular vesicles can be stored long term, for example, for 1, 2, 3, 4, 5, 6, 12, 24, 36, or 48 months or longer, for example, at −80° C., and then accessed when required.

As used herein, the term "extracellular vesicles" or "EVs" refers to subcellular lipid vesicles related by a variety of cell types. EVs include exosomes (30-200 nm), microvesicles (50-1000 nm), and apoptotic bodies (500-2000 nm). Without wishing to be bound by theory, it is believed that all 3 groups of EVs may contribute to the therapeutic effects described herein.

As used herein, the term "exosomes" (30-200 nm) refers to a subgroup of small lipid vesicles released by a variety of cell types. Exosomes are generated by inward- or reverse budding, resulting in particles that contain cytosol and exposed extracellular domains of certain membrane-associated proteins (Stoorvogel et al., *Traffic* 3:321-330 (2002)). Methods of preparing exosomes from cells are known in the art. See, for example, Raposo et al., *J. Exp. Med.* 183:1161 (1996). In one method, exosomes are recovered from conditioned culture medium by centrifugation. Exosomes suited for use in the methods can be derived fresh or can be previously frozen and thawed. In some embodiments, exosome preparations may also include micro-vesicles.

Exosomes can have, but are not limited to, a diameter of about 10-300 nm. In some embodiments, the exosomes can have, but are not limited to, a diameter between 20-250 nm, 30-200 nm, or about 50-150 nm. Exosomes may be isolated or derived from any cell type that resides in the target tissue of interest which can be isolated and cultured for a period of time appropriate for the isolation of exosomes.

As used herein, "cold atmospheric plasma" or "CAP" refers to a substance that can be produced at atmospheric pressure when a carrier gas is ionized as it moves between two electrodes with a high voltage current applied to them. Examples of carrier gases that can be used to make CAP include helium, argon, nitrogen, oxygen, air, and other gases and the mixtures thereof. CAP contains populations of reactive oxygen and/or reactive nitrogen species or "RONS."

As used herein, when a substance has been "CAP-modified" or "CAP-treated" or "CAP-activated," which terms are synonymous and can be used interchangeably herein, the substance, such as a tissue sample, CSF, or a population of isolated extracellular vesicles has been exposed to CAP for a length of time to impart a chemical and/or physical change to the substance. CAP is known to be a source of various physical and chemical entities, namely, RONS, electric charges, electric and magnetic fields, and photons. Any controllable physical, chemical, and/or physicochemical modification of the exposed substance can lead to its modified functionalities leading to selective cytotoxicity against cancer cells. For instance, exosomes are one class of extracellular vesicles that comprise of phospholipid bilayer, proteins, DNA, RNA, etc., therefore, the likely modifications of the exosomes are, but not limited to, lipid peroxidation, (chemical) oxidations of protein, DNA, RNA by CAP-induced RONS, and (physical) electroporation. The latter is a physical modification in which via the high electric field of CAP jet devices induces small pores in the membrane of exosome suspended in a conductive solution. As a result, these controllable modifications of exosomes result in favorable modified cell-to-cell communication (e.g., mitochondrial and/or receptor cell death signaling pathways) in the tumors triggering apoptotic cell death. In some embodiments, a substance can be "CAP-modified" when the substance is exposed to CAP for an optimized exposure time (e.g., about 1 to about 10 minutes) that depends specifically on the substance and its volume to be treated and the operation condition of the CAP jet devices to be optimized.

In some embodiments, extracellular vesicles that have been CAP-modified can contain modifications to their structures, as described above (e.g., phospholipid bilayer, proteins, DNA, RNA, etc.) that can be attributable to the various physical and chemical entities from CAP treatment. For example, modifications to extracellular vesicle structures can be caused by short-lived RONS, such as hydroxyl radical (HO), atomic oxygen (O), superoxide radical anion ($O_2$) and the related hydroperoxyl radical (HOO), singlet oxygen ($^1O_2$), ozone ($O_3$), nitrogen oxide and dioxide (NO, $NO_2$), and peroxynitrous acid (ONOOH) or its anion ($ONOO^-$).

In some embodiments, CAP-modified extracellular vesicles can also carry long half-life RONS such as hydrogen peroxide ($H_2O_2$, formed from a primary HO), nitrite and nitrate ions ($NO_2^-$ and $NO_3^-$, formed from primary NO, $NO_2$, $NO_3$). Such long-life RONS can be stable for one or more days and even longer.

In some embodiments, a bubbling mixing method can be employed that uses a gas such as (but not limited to) helium, argon, oxygen, nitrogen, and an appropriate mixture of these gases during CAP treatment with a CAP jet as shown and described in FIGS. 1-3 (described below). As shown in FIGS. 4-7, the bubbling gas can be controlled to flow at a rate in the range of about 0 mL/min to about 100 mL/min through an electrically insulating capillary of micrometers in diameter that is submerged vertically into the liquid container of the extracellular vesicles. Bubbles of the sizes in the range of micrometers to millimeters are generated at the tip of the capillary located near the bottom of the container and rise to the liquid surface. The rising of the bubbles results in the uniform mixing of the CAP-modified extracellular vesicles and redistribute uniformly the long-life RONS to modify the extracellular in the whole bulk of the liquid. Thus, this bubble mixing method is employed to improve the quality of CAP-modified extracellular vesicles.

As used herein, the terms "treat" and "treating" refer to therapeutic measures, wherein the object is to slow down or alleviate (lessen) an undesired physiological change or pathological disorder resulting from a disease, as described herein, such as cancer. For purposes of this invention, treating the disease includes, without limitation, alleviating one or more clinical indications, reducing the severity of one or more clinical indications of the disease, diminishing the extent of the condition, stabilizing the subject's disease (i.e., not worsening), delay or slowing, halting, or reversing the disease and bringing about partial or complete remission of the disease. Treating the disease can also include prolonging survival by days, weeks, months, or years as compared to prognosis if treated according to conventional medical practice.

As used herein, the terms "subject" or "patient" or "individual" are used interchangeably and can encompass any vertebrate, including, without limitation, humans, mammals, reptiles, amphibians, and fish. However, advantageously, the subject or patient is a mammal such as a human, or a mammal such as a domesticated mammal, e.g., dog, cat, horse, and the like, or livestock, e.g., cow, sheep, pig, and the like. In exemplary embodiments, the subject is a human. As used herein, the phrase "in need thereof" indicates the state of the subject, wherein therapeutic or preventative measures are desirable. Such a state can include, but is not limited to, subjects having a disease such as cancer, as described herein, or a pathological symptom or feature associated with the disease.

Treatment

In some embodiments, a method of treating an individual for GBM or other cancer includes obtaining a sample of CSF from the individual, isolating extracellular vesicles from the CSF sample, activating the isolated extracellular vesicles with CAP, and administering the CAP-modified extracellular vesicles to the individual. The administration of CAP-modified extracellular vesicles to the individual treats the individual's GBM.

In other embodiments, a method of treating an individual for cancer can include obtaining a sample for isolating extracellular vesicles, wherein the sample is obtained from a cancerous tumor or a tissue of cancer origin. For example, the cancer may be a type of liver cancer, and the sample obtained (e.g., biopsied, excised, etc.) can be from a cancerous liver tumor or a non-cancerous, healthy portion of the liver. In some instances, a sample may contain only cancer cells. In some instances, a sample may contain cancerous tissues, which can include cancer cells and non-cancerous cells derived from the same tissue (i.e., a tissue of cancer cell origin). It is also contemplated that samples may contain other cell types commonly found in tissues (e.g., blood cells, etc.). In still further instances, contemplated samples can be obtained from cells or tissues that have been differentiated from pluripotent stem cells (embryonic and/or induced) into a tissue type where a cancer to be treated has arisen. In other words, a tissue of cancer cell origin can be produced from an embryonic or induced pluripotent stem cell.

Compositions

In some cases, a method of treating or preventing a disease or injury as described herein comprises administering a pharmaceutical composition comprising a therapeutically effective amount of CAP-modified extracellular vesicles (i.e., for therapeutic applications). As used herein, the term "pharmaceutical composition" refers to a chemical or biological composition suitable for administration to a subject. Examples of compositions appropriate for such therapeutic applications include preparations for parenteral, subcutaneous, transdermal, intradermal, intramuscular, intracoronarial, intramyocardial, intraperitoneal, intravenous or intraarterial (e.g., injectable), or intratracheal administration, such as sterile suspensions, emulsions, and aerosols. Intratracheal administration can involve contacting or exposing lung tissue, e.g., pulmonary alveoli, to a pharmaceutical composition comprising a therapeutically effective amount of CAP-modified extracellular vesicles.

In some cases, pharmaceutical compositions appropriate for therapeutic applications may be in admixture with one or more pharmaceutically acceptable excipients, diluents, or carriers such as sterile water, physiological saline, glucose or the like. For example, CAP-modified extracellular vesicles described herein can be administered to a subject as a pharmaceutical composition comprising a carrier solution.

Formulations may be designed or intended for oral, rectal, nasal, topical or transmucosal (including buccal, sublingual, ocular, vaginal and rectal) and parenteral (including subcutaneous, intramuscular, intravenous, intraarterial, intradermal, intraperitoneal, intrathecal, intraocular and epidural) administration. In general, aqueous and non-aqueous liquid or cream formulations are delivered by a parenteral, oral or topical route. In other embodiments, the compositions may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot. In some cases, pharmaceutical compositions are lyophilized. In other cases, pharmaceutical compositions as provided herein contain auxiliary substances such as wetting or emulsifying agents, pH buffering agents, gelling or viscosity enhancing additives, preservatives, flavoring agents, colors, and the like, depending upon the route of administration and the preparation desired. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

The preferred route of administration may vary with, for example, the subject's pathological condition or weight or the subject's response to therapy or that is appropriate to the circumstances. The formulations can also be administered by two or more routes, where the delivery methods are essentially simultaneous or they may be essentially sequential with little or no temporal overlap in the times at which the composition is administered to the subject.

Suitable regimes for initial administration and further doses or for sequential administrations also are variable, may include an initial administration followed by subsequent administrations, but nonetheless, may be ascertained by the skilled artisan from this disclosure, the documents cited herein, and the knowledge in the art.

In some cases, CAP-modified extracellular vesicles may be optionally administered in combination with one or more additional active agents, including chemotherapeutic agents (alkylating agents, antimetabolites, and topoisomerase inhibitors), targeted therapy agents (tyrosine kinase inhibitors, monoclonal antibodies, and angiogenesis inhibitors), immunotherapy agents (checkpoint inhibitors, cancer vaccines, and adoptive cell therapy), and hormone therapy. When administered in combination with one or more active agents, CAP-modified extracellular vesicles can be administered either simultaneously or sequentially with other active agents. Additional contemplated active agents could include cellular therapies such as chimeric antigen receptor T cells, cytokines, and bispecific T cell engagers. Combinations of such additional active agents are also contemplated for use herein.

In some embodiments, CAP-modified extracellular vesicles are administered to a subject in need thereof using an infusion, topical application, surgical transplantation, or implantation. In an exemplary embodiments, administration is systemic. In such cases, CAP-modified extracellular vesicles can be provided to a subject in need thereof in a pharmaceutical composition adapted for intravenous administration to subjects. Typically, compositions for intravenous administration are solutions in sterile isotonic aqueous buffer. The use of such buffers and diluents is well known in the art. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of the active agent. Where the composition is to be administered by infusion, it can be dispensed with an infusion bottle containing sterile pharmaceutical-grade water or saline. Where the composition is administered by injection, an ampoule of sterile water for injection or saline can be provided so that the ingredients may be mixed prior to administration. In some cases, compositions comprising CAP-modified extracellular vesicles are cryopreserved prior to administration.

Therapeutically effective amounts of CAP-modified extracellular vesicles can be re-administered to a subject in need thereof. An effective dose or amount is an amount sufficient to effect a beneficial or desired clinical result. With regard to the methods of the present invention, the effective dose or amount, which can be administered in one or more administrations, is the amount of CAP-modified extracellular vesicles sufficient to elicit a therapeutic effect in a subject to whom the cells are administered. In some cases, an effective dose of EVs is about $1\times10^5$ extracellular vesicles/kilogram to about $1\times10^{14}$ extracellular vesicles/kilogram body weight of the recipient. In another embodiment, a therapeutically effective amount of CAP-modified EVs is about $1\times10^{11}$ to about $1\times10^{14}$ EV/kg. In one particular embodiment, a therapeutically effective amount of CAP-modified EVs is administered to a subject in a dose of about $2\times10^{10}$/kg. Effective amounts will be affected by various factors that modify the action of the cells upon administration and the subject's biological response to the cells, the patient's age, sex, and diet, time of administration, and other clinical factors, such as type of cancer being treated.

Therapeutically effective amounts for administration to a human subject can be determined in animal tests and any art-accepted methods for scaling an amount determined to be effective for an animal for human administration. For example, an amount can be initially measured to be effective in an animal model (e.g., to achieve a beneficial or desired clinical result). The amount obtained from the animal model can be used in formulating an effective amount for humans by using conversion factors known in the art. The effective amount obtained in one animal model can also be converted for another animal by using suitable conversion factors such as, for example, body surface area factors.

It is to be understood that, for any particular subject, specific dosing regimes can be adjusted over time according to the individual need and the professional judgment of the person administering or supervising the administration of the CAP-modified extracellular vesicles. For example, the dosage for a particular subject with a disease to be treated can be increased if the lower dose does not elicit a detectable or sufficient improvement in one or more symptoms of the disease. Conversely, the dosage can be decreased if the disease is treated or eliminated.

In some cases, therapeutically effective amounts of CAP-modified extracellular vesicles can be determined by, for example, measuring the effects of a therapeutic in a subject by incrementally increasing the dosage until the desired symptomatic relief level is achieved. A continuing or repeated dose regimen can also be used to achieve or maintain the desired result. Any other techniques known in the art can be used as well in determining the effective amount range. Of course, the specific effective amount will vary with such factors as the particular disease state being treated, the physical condition of the subject, the type of animal being treated, the duration of the treatment, and the nature of any concurrent therapy.

In any of the methods of the present invention, the donor and the recipient of the CAP-modified extracellular vesicles can be a single individual, autologous, or different individuals, for example, allogeneic or xenogeneic individuals. As used herein, the term "allogeneic" refers to something that is genetically different although belonging to or obtained from the same species (e.g., allogeneic tissue grafts or organ transplants). "Xenogeneic" means the cells could be derived from a different species. In one embodiment, extracellular vesicles can be collected from patients and CAP-modified to be given freshly to a person following or concurrently with chemotherapy. In some embodiments, any allogeneic donor may act as a universal third-party donor.

Device

In one non-limiting example of the present disclosure, CAP-modified extracellular vesicles can be generated using a CAP jet described below. FIG. 1 depicts a cold atmospheric plasma (CAP) jet 100 for the application of plasma cancer treatment. The CAP jet 100 includes a dielectric tube 102 such that the dielectric tube is a glass tube, a quartz tube, or the like. The dielectric tube 102 may have a designated length, such as 160 mm long. However, any suitable length is contemplated herein, such as about 20, 30, 40, 50, 60, 70, 80, 90, 100, 120, 140, 160, 180, 200, 240, 280, 300, or 400 mm. The CAP jet 100 has an outer diameter 104 and an inner diameter 106. In some embodiments, the outer diameter 104 is 4.2 mm and the inner diameter 106 is 2.4 mm. However, any suitable outer diameter is contemplated herein, such as about 2.0, 3.0, 4.0, 5.0, 6.0, 7.0, 8.0, 9.0, 10.0 mm and any suitable inner diameter is also contemplated such as about 1.0, 1.2, 1.4, 1.6, 1.8, 2.0, 3.0, 4.0, 5.0, 6.0, 7.0, 8.0, 9.0 mm. The inner diameter 106 defines an interior of the dielectric tube 102 configured to receive a stream of a feed gas 122. In some embodiments, the feed gas 122 is helium gas. Other types of feed gas are possible, such argon, nitrogen, helium, water vapor, air, and a controlled compositional mixture of them.

The feed gas 122 is stored in a gas tank 124, and the gas tank 124 supplies the feed gas 122 through a gas tubing system 126 such that the feed gas 122 is configured to flow from the gas tank 124, through the gas tubing system 126, and into the interior of the dielectric tube 102. In some embodiments, the gas tubing system 126 further includes a gas regulator 128 such that the gas regulator 128 regulates the feed gas 122 before it is fed into the interior of the dielectric tube 102. A flow meter 130 is positioned between the gas tank 124 and the gas tubing system 126 such that the flow meter 130 controls the flow rate of the feed gas 122 through the gas tubing system 126.

The CAP jet 100 also includes a high-voltage power supply 108. An output 110 of the high voltage power supply 108 is electrically connected to an internal pin or wire electrode 112 such that the internal pin or wire electrode 112 at least partially extends into the interior of the dielectric tube 102. In some embodiments, the internal electrode 112 extends into the interior of dielectric tube 102 and ends at a location of about 0 mm to about 20 mm from the downstream nozzle (orifice) of the dielectric tube 102. An external coil or wire electrode 114 wraps around a lower portion of the outer diameter 104 of the dielectric tube 102. In some embodiments, the external electrode 114 wraps around about a 1 to 10 mm portion of the outer diameter 104 of the dielectric tube 102 whose downstream nozzle/orifice begins about 1 to 10 mm lower than the external electrode 114. The external electrode 114 is coupled to the dielectric tube 102 by use of an O-ring gasket 116. The external electrode 114 is also grounded through a resistor 118 to limit the current in to less than approximately 10 mA so that arcing is prevented. In some embodiments, the resistor 118 is a 100 MΩ resistor, but other resistors having greater or less are resistance herein. In some embodiments, both the internal electrode 112 and the external electrode 114 are electrically insulated. The material and thickness of electrical insulation coating is chosen so that it can withstand the hostile ionizing chemistry and physics of CAP. For instance, it may be chosen to be an aromatic polyimide resin coating of about 0.043 mm in thickness. Additional suitable materials and corresponding thicknesses can be used.

Figure 2:
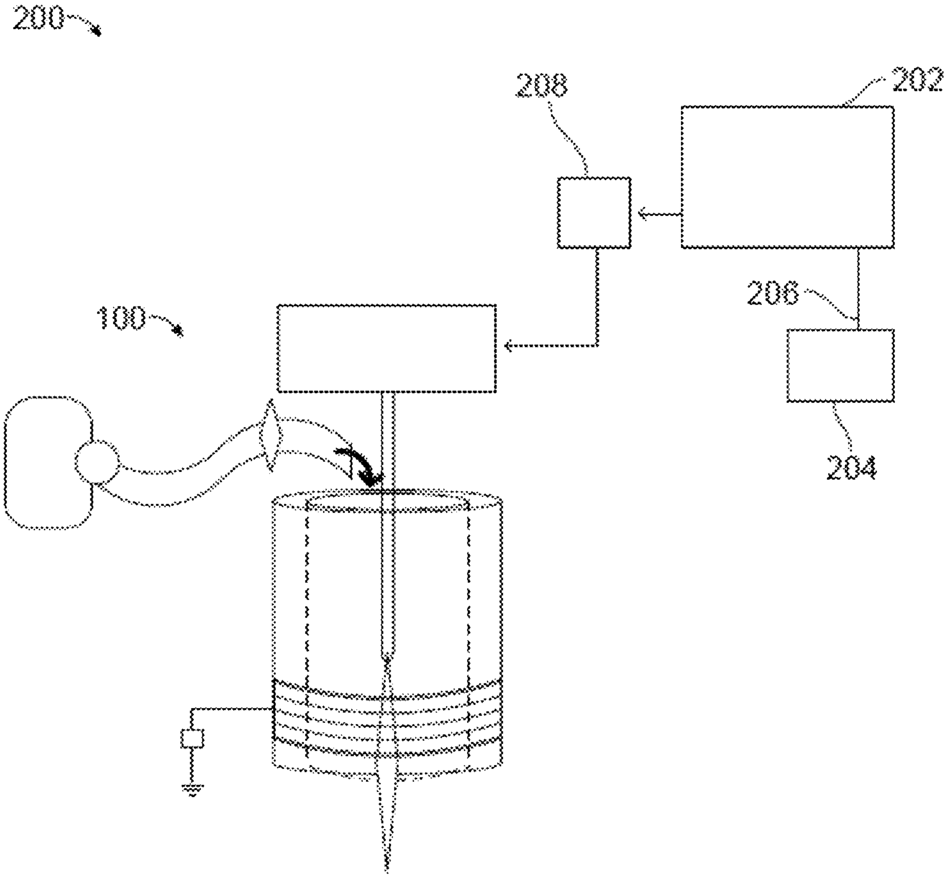
FIG. 2 is a perspective view of a cold atmospheric plasma (CAP) jet for application of plasma cancer treatment, according to an exemplary embodiment of the present disclosure.

FIG. 2 depicts a cold atmospheric plasma (CAP) jet 200 for application of plasma cancer treatment. The CAP jet 200 includes all of the components of the CAP jet 100 in conjunction with additional components of the high-voltage power supply 108. The high-voltage power supply 108 could further include a computer 202 such that a program running on the computer 202 is used to communicate with other components of the high-voltage power supply 108 and to control the CAP jet 200 device operation. In some embodiments, a signal generator 204 is connected to the computer 202 via a high-speed USB-adapted cable 206 (other connectors contemplated herein) such that the signal generator 204 is a pulse/function generator that receives one or more commands from the program on the computer 202 such that the one or more commands define a series of output signals having various function waveforms based on the one or more commands. A high-voltage amplifier 208 may also be configured to receive the series of output signals from the signal generator 204 through the computer 202 and amplify each output signal of the series of output signals to the high voltages that can break down the feed gas 122 to make dielectric discharges.

Figure 3:
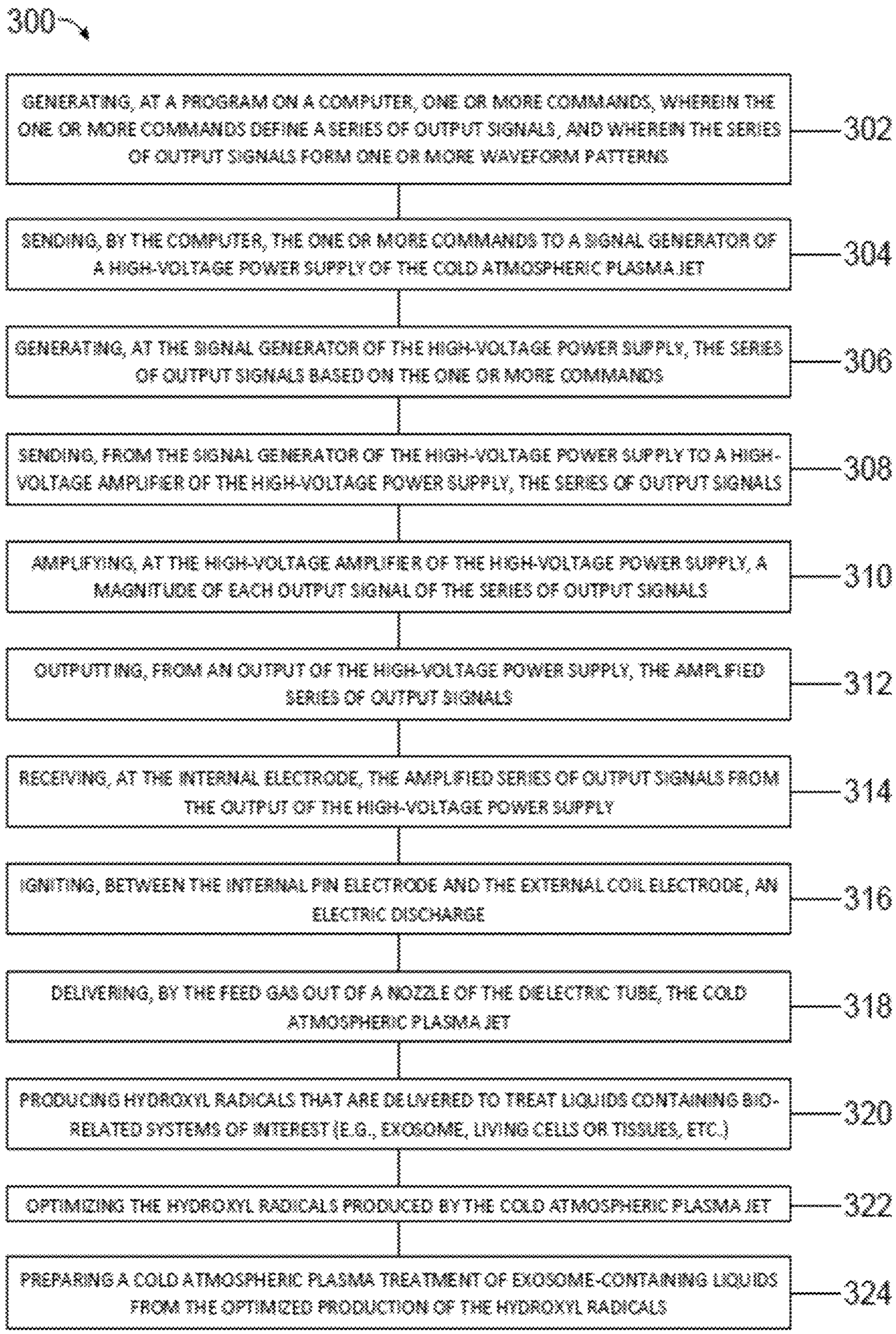
FIG. 3 is a block diagram of a method of using a cold atmospheric plasma jet, according to an exemplary embodiment of the present disclosure.
Figure 4:
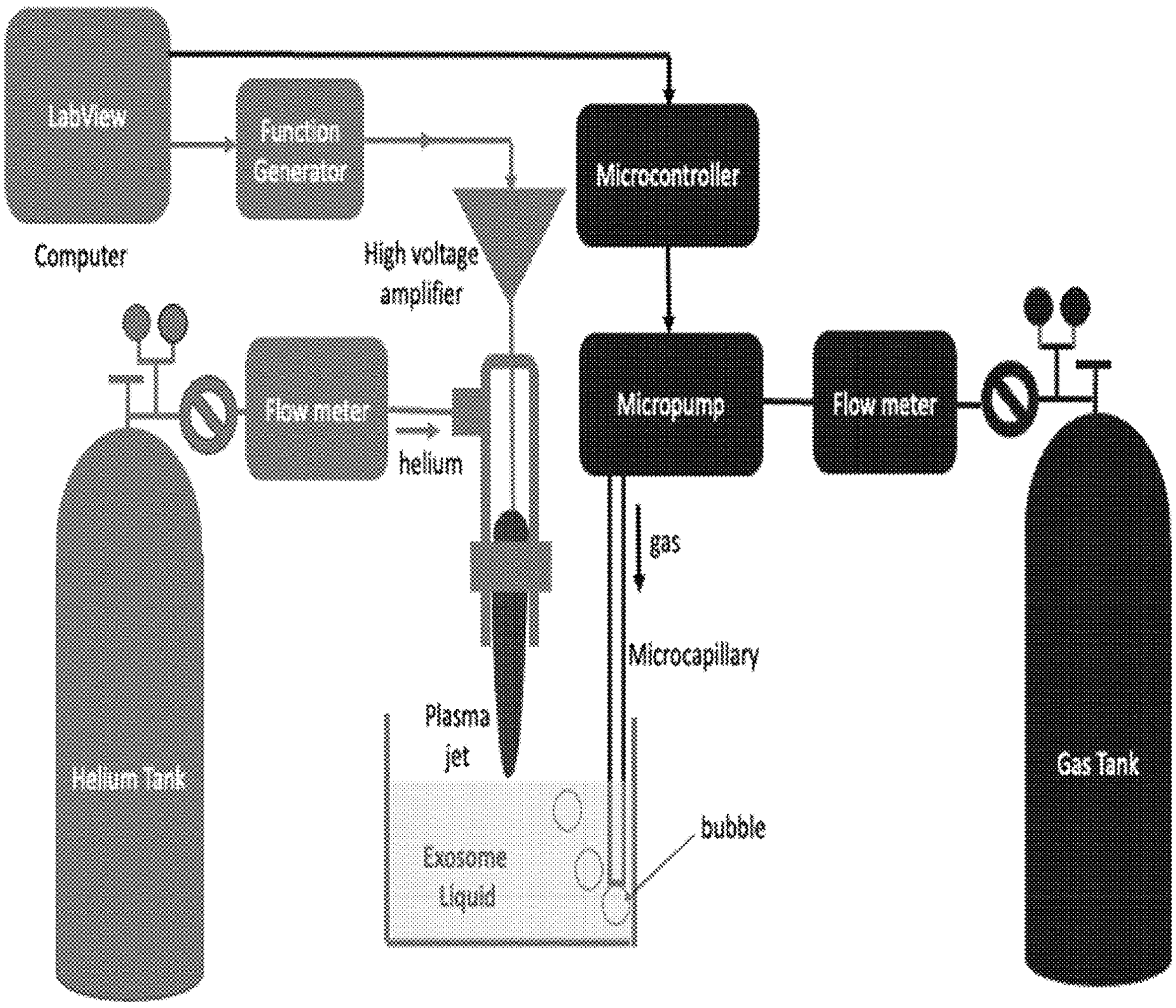
FIG. 4 is a depiction of an integrated apparatus to improve the CAP-modified extracellular vesicles such as exosomes for cancer treatment.
Figure 5:
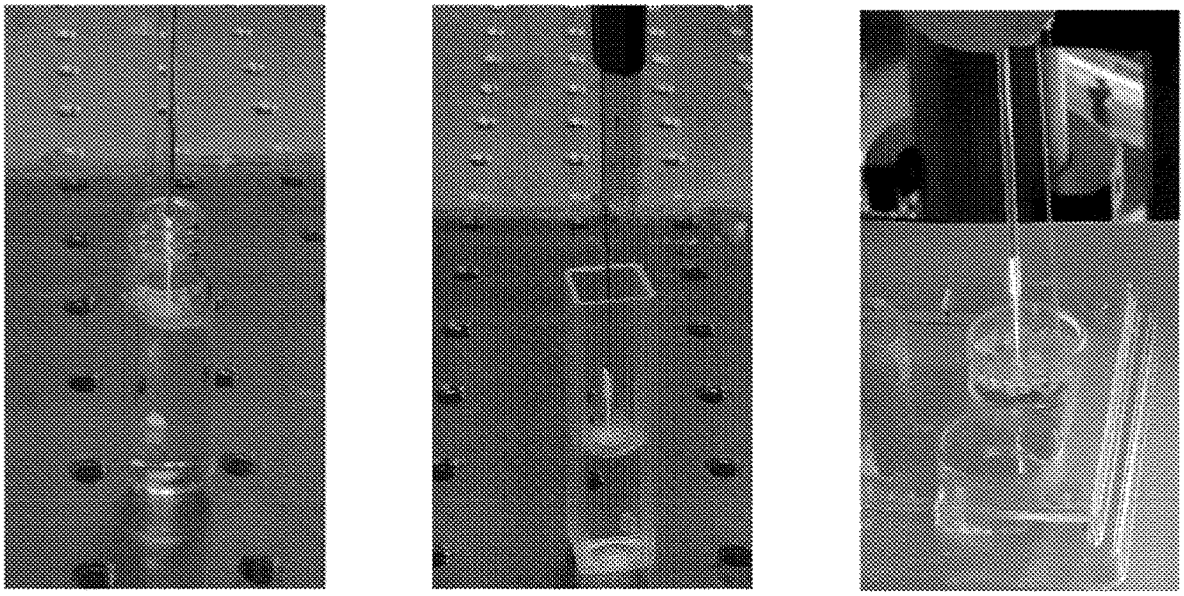
FIG. 5 shows different configurations of integrated systems of gas-bubble mixing coupled to a CAP jet.
Figure 6:
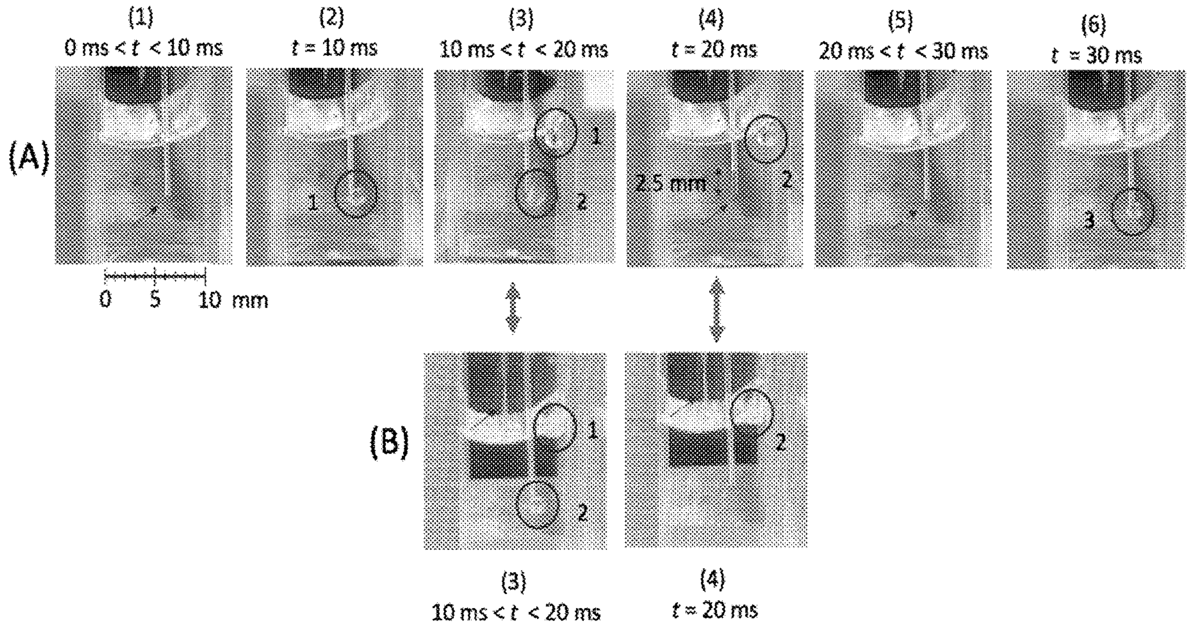
FIG. 6 demonstrates gas bubble formation, rise in, and break-up in a gas-plasma-liquid system controlled by injecting air into a submillimeter microcapillary. (A) plasma is off, and (B) plasma is on. Circles indicate bubbles.
Figure 7:
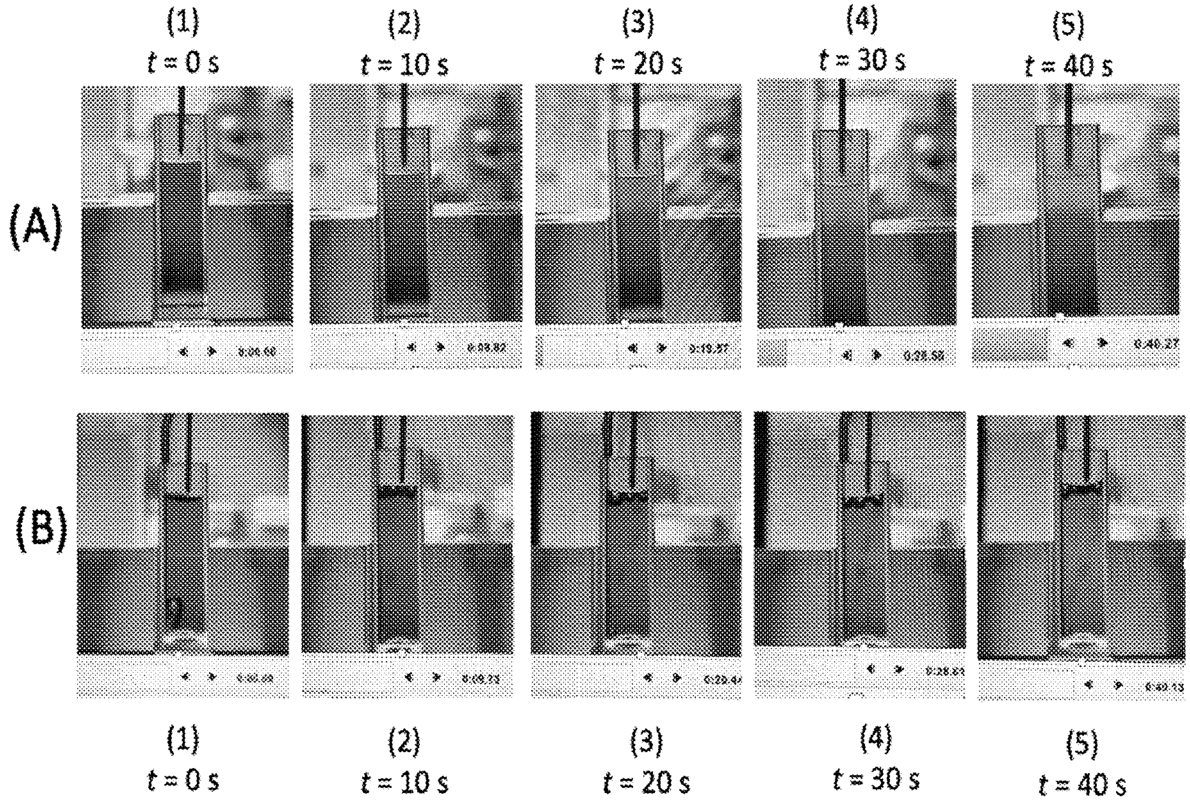
FIG. 7 demonstrates alteration of the pH value of the solution of bromophenol blue dye dissolved in distilled water treated with CAP (A) and without (B) with gas bubble mixing. The blue and yellow colors indicate the neutral pH value (pH=7) (darker) and acidic pH value (lighter) (pH<3), respectively.

FIG. 3 depicts a block diagram of a method of using a cold atmospheric plasma jet.

At step 302, the method includes generating, at a program on a computer, one or more commands, wherein the one or more commands define a series of output signals, and wherein the series of output signals form one or more waveform patterns.

At step 304, the method includes sending, by the computer, the one or more commands to a signal generator of a high-voltage power supply of the cold atmospheric plasma jet, wherein the cold atmospheric plasma jet comprises a dielectric tube having an outer diameter and an inner diameter, wherein the inner diameter defines an interior of the dielectric tube, and wherein the interior of the dielectric tube is configured to receive a stream of a working gas. An internal pin or wire electrode that at least partially extends into the interior of the dielectric tube, wherein the internal electrode is electrically connected to an output of the high-voltage power supply. An external coil or wire electrode that wraps around a lower portion of the outer diameter of the dielectric tube, wherein the external electrode is mounted on the dielectric tube by using an O-ring gasket, and wherein the external electrode is grounded through a resistor. The internal electrode and the external electrode are each electrically insulated.

At step 306, the method includes generating, at the signal generator of the high-voltage power supply, the series of output signals based on the one or more commands.

At step 308, the method includes sending, from the signal generator of the high-voltage power supply to a high-voltage amplifier of the high-voltage power supply, the series of output signals.

At step 310, the method includes amplifying, at the high-voltage amplifier of the high-voltage power supply, a magnitude of each output signal of the series of output signals.

At step 312, the method includes outputting, from an output of the high-voltage power supply, the amplified series of output signals.

At step 314, the method includes receiving, at the internal electrode, the amplified series of output signals from the output of the high-voltage power supply.

At step 316, the method includes igniting, between the internal pin electrode and the external coil electrode, an electric discharge.

At step 318, the method includes delivering, by the feed gas or gases out of a nozzle of the dielectric tube, the cold atmospheric plasma jet.

At step 320, the method includes producing hydroxyl radicals that are delivered to treat liquids containing bio-related systems of interest (e.g., exosome, living cells or tissues, etc.).

At step 322, the method includes optimizing the hydroxyl radicals produced by the cold atmospheric plasma jet.

At step 324, the method includes preparing a cold atmospheric plasma treatment of exosome-containing liquids from the optimized production of the hydroxyl radicals.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present invention has been described in terms of one or more preferred embodiments, and it should be appreciated that many equivalents, alternatives, variations, and modifications, aside from those expressly stated, are possible and within the scope of the invention.

EXAMPLES

Example 1: Modification of Extracellular Vesicles Including Exosomes in Cerebral Spinal Fluid Using Cold Atmospheric Plasma as a Treatment for Glioblastoma Introduction:

Glioblastoma (GBM) is one of the most deadly and recalcitrant solid cancers, with an overall 5-year survival rate of 10% (1). The current treatment for GBM includes maximal safe resection, followed by radiation therapy and concomitant chemotherapy with temozolomide (TMZ), and finally, with adjuvant TMZ. Despite recent medical advances, most GBM patients experience recurrence by 8 months (2).

Exosomes are a type of extracellular vesicle that are secreted by all cell types upon fusion of a multi-vesicular body with the plasma membrane (3). Exosomes are generally considered to be produced through the inward budding of late-stage endosomes, forming multi-vesicular bodies, which then release these vesicles into the extracellular space upon fusion with the plasma membrane (4). Currently exosomes are believed to play a major role in cell-to-cell communication, such as tumor and stromal cell communication and signaling, as they carry genetic materials, proteins and other important molecules (5, 6). When fusing with recipient cells, exosomes also fuse their lipid membranes, including cholesterol, sphingomyelin, ceramide, and various lipid molecules, with the recipient cell membrane (7, 8). Exosomes from tumor cells have generally been described as playing a role in promoting tumor activation, growth and metastasis (9, 10). However, there is also evidence that exosomes can be modified to inhibit tumor growth (11, 12).

Cold atmospheric plasma (CAP) contains dozens of reactive oxygen and nitrogen species (RONS), which are produced at atmospheric pressure when a carrier gas is ionized as it moves between two electrodes with a high voltage current applied to them, enabling its use in biomedicine (13, 14). Compared to normal, healthy cells, cancer cells are particularly sensitive to RONS; hence, harnessing CAP-generated RONS for cancer therapy has recently garnered increased attention (15, 16). A major obstacle in applying CAP in clinical settings is the limit in depth of tissue penetration by CAP when it is applied directly. Here, methods to apply CAP in systemic treatments are established.

Material and Methods:

A portable cold atmospheric plasma (CAP) device was employed in the protocol. The device can be employed in surgical settings. After evaluating a variety of gases including helium, argon, nitrogen, and air, helium was identified as the most effective for generating CAP and used herein, as described below.

The CAP device was constructed using a glass tube that served as a dielectric barrier for the gas jet. A grounded electrode was located outside the glass tube, apart from the high-voltage electrodes. Helium was used as the working gas with various flow rates. The CAP device was powered by a high-voltage power supply, which consists of a signal generator and a high-voltage amplifier. The high-voltage values ranged from −10 kV to +10 kV. In addition, the range of frequencies for the input signal of the amplifier was from 5 mHz to 23 kHz. In this work, a sinusoidal waveform was used for the high voltage between the two electrodes with various values of the voltage amplitude and of frequency.

CSF:

Cerebral spinal fluid (CSF), which is a naturally occurring fluid surrounding the brain, was obtained from donors without cancer via IRB-approved protocol. CSF was then treated with CAP for various durations from 2 to 6 minutes, then transferred to human glioblastoma cells (SJ-GBM2) in various volumes.

Exosomes:

To determine the role of exosomes may play in CAP-modified CSF, the therapeutic effects of CAP-treated CSF with and without its exosomes on both normal astrocytes (NHA) and human glioblastoma cell lines (SJ-GBM2 and U87) were examined. Fetal bovine serum (FBS) and exosome-free FBS were used as controls. Extracellular vesicles (EVs) were isolated directly from biological fluid (CSF) using a modified two-step centrifugation process as described by Thery C. et al. Curr Protoc Cell Biol (2006).

Dose Response:

In a subsequent experiment, exosomes were removed from CSF (and FBS, as a control) by ultracentrifugation. The exosomes were then quantified to determine the concentration that was originally from CSF or control. After that, the exosomes were added back into the exosome-free CSF or FBS and each was treated with CAP and then administered to GBM cell lines.

Figure 8:
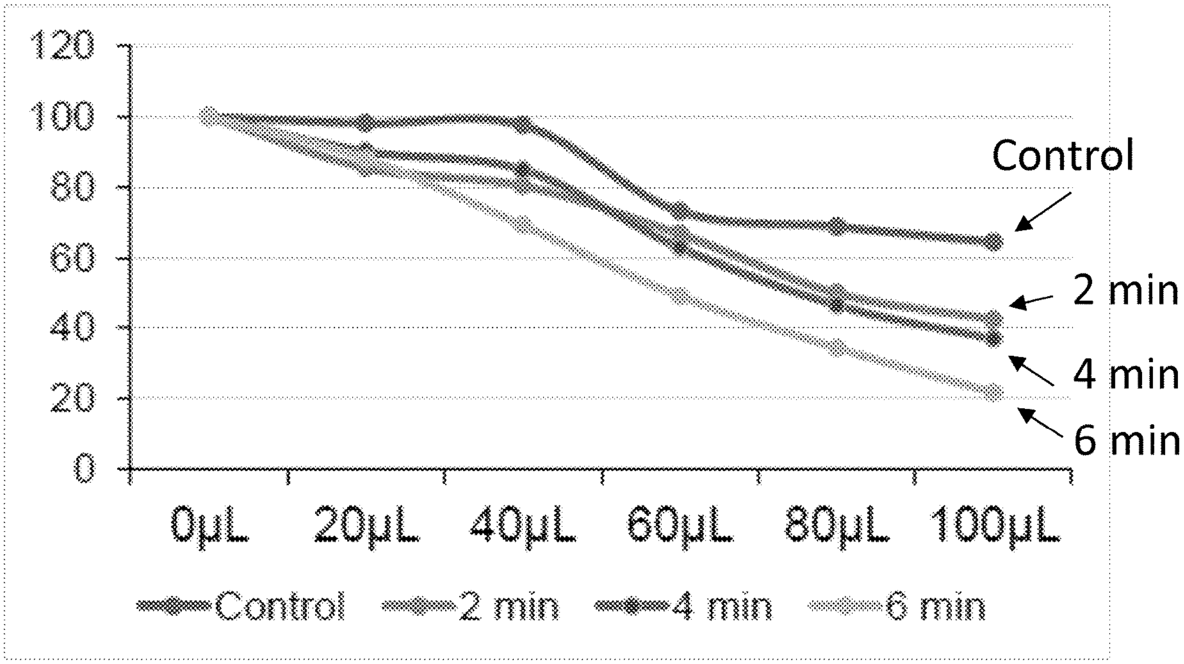
FIG. 8: Cell viability of human glioblastoma cell (SJ-GBM2) treated with CAP-modified CSF demonstrate at different durations and volumes. The maximum % of cell death was seen after the addition of 100 μL of 6 min CAP treated CSF to the glioma cells which was p<0.001 when compared to the corresponding controls. Two minutes and 4 minutes of CAP treatment also caused a significant cell death as well (p<001 for both) compared to control. These results established that CAP treated CSF could kill cancer. They clearly indicate that CAP treated CSF could kill cancer cells in a dose and duration-dependent manner.

Results:

CSF:

As shown in FIG. 8, a dose-dependent, inverted relationship was observed between the amount of treated CSF administered, the duration of treatment, and the tumor cell viability.

Figure 9A:
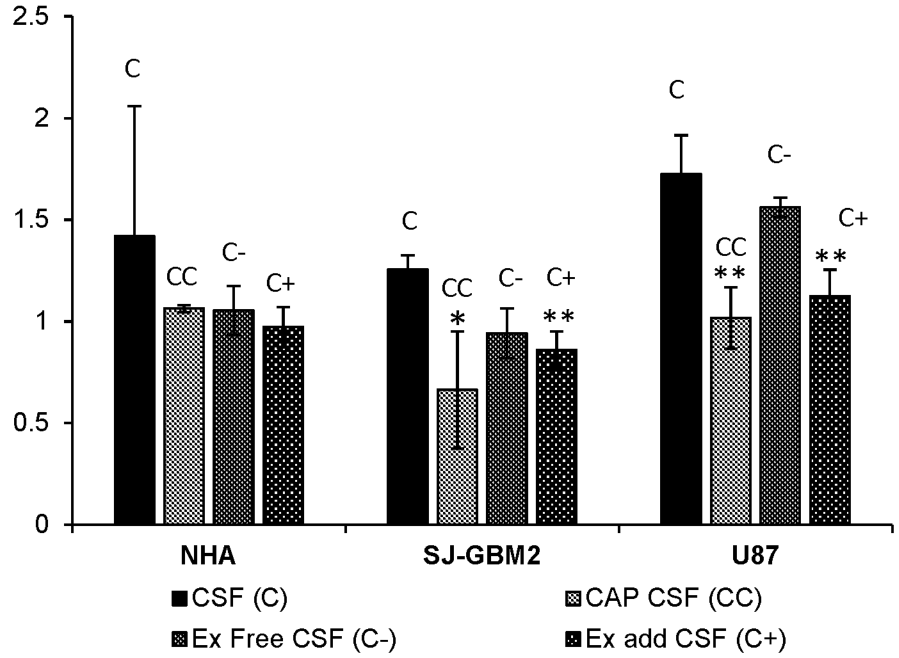
FIGS. 9A-9B: CAP-treated extracellular vesicles increase cell death in glioblastoma.
Figure 9B:
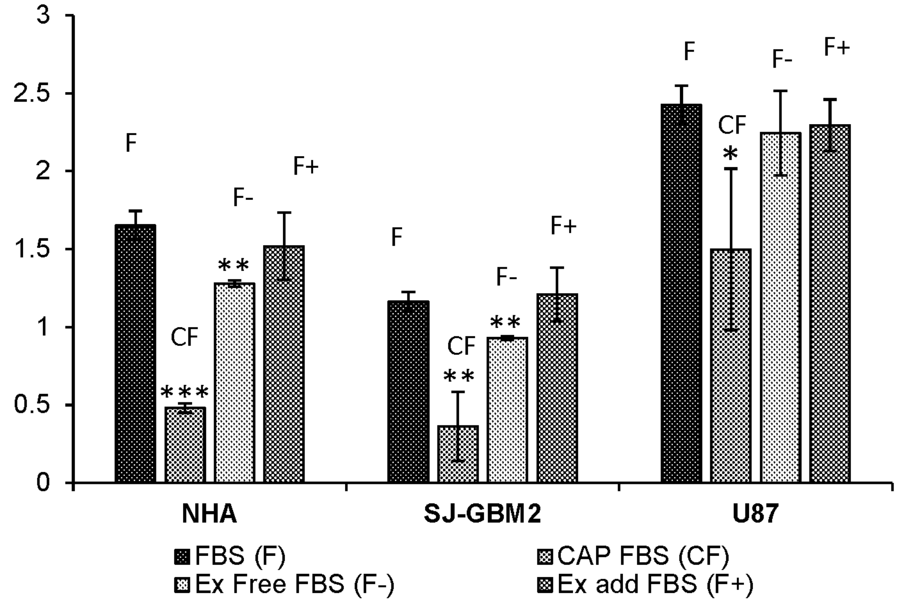

Exosomes:

Next, as shown in FIGS. 9A-9B, CAP-treated CSF without exosomes had no significant effect on tumor cell viability. However, when exosomes were added back to exosome-free CSF, the tumor-killing effect was partially restored. These effects were not seen using FBS and exosome-free FBS.

Figure 10A:
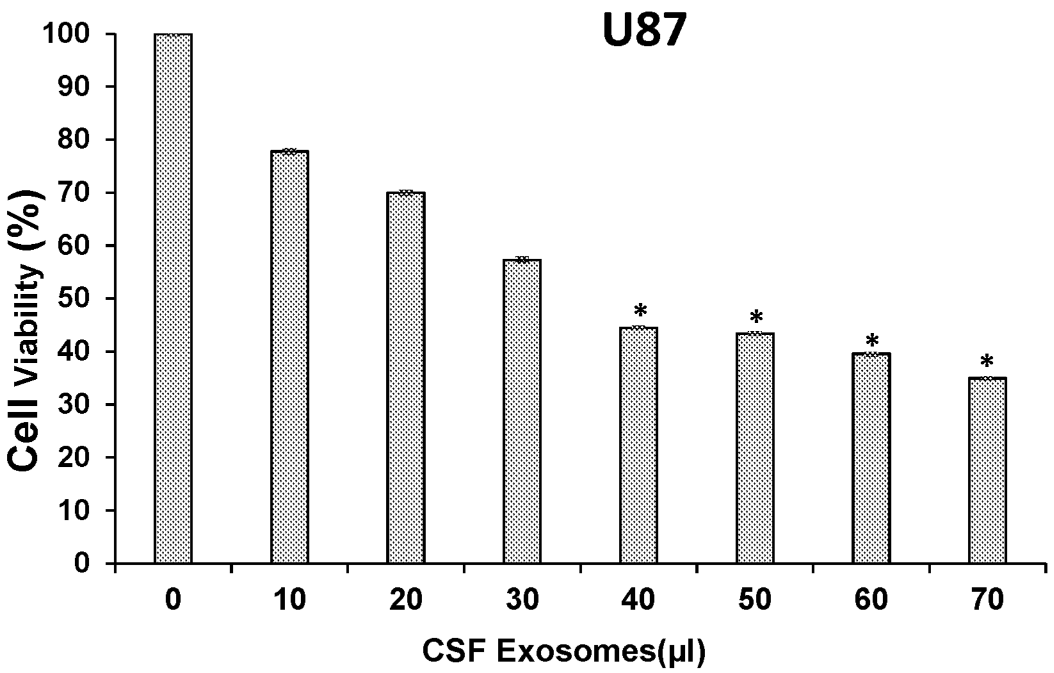
FIGS. 10A-10B: Dose-dependent CAP-treated extracellular vesicles increase cell death in glioblastoma.
Figure 10B:
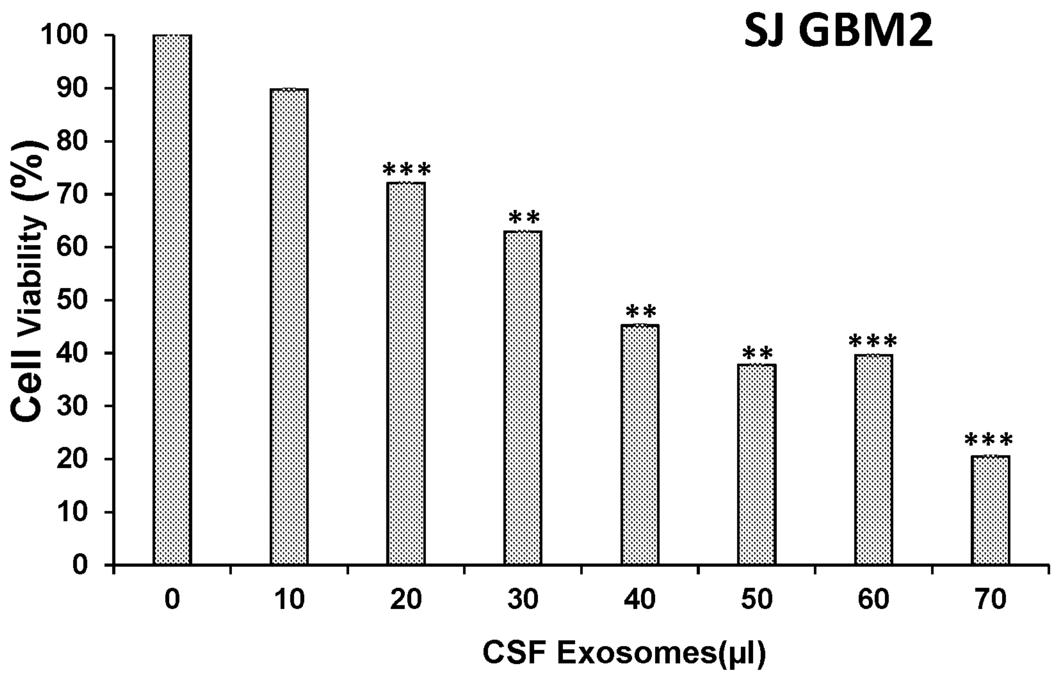

Dose Response:

Next, exosomes derived from CSF were observed to have dose-dependent effects on two human glioblastoma cell lines (SJ-GBM2 and U87) (FIGS. 10A-10B).

Conclusion:

The results from these experiments show that exosomes from CSF can be isolated and treated with CAP to have a cytotoxic effect on GBM cell lines. The results demonstrate the utility of using CAP-modified exosomes as a therapeutic agent for systemic treatment of diseases, such as GBM.

Example 2: Comparative Analysis of CAP-Modified Exosomes from Different Sources Introduction:

This example is a comparative analysis of the cold atmospheric plasma (CAP)-modified exosomes from different sources like cerebrospinal fluid (CSF), mesenchymal stromal cells (MSCs), human astrocytes (NHAs), and human glioblastoma cells (GBMs).

Figure 11A:
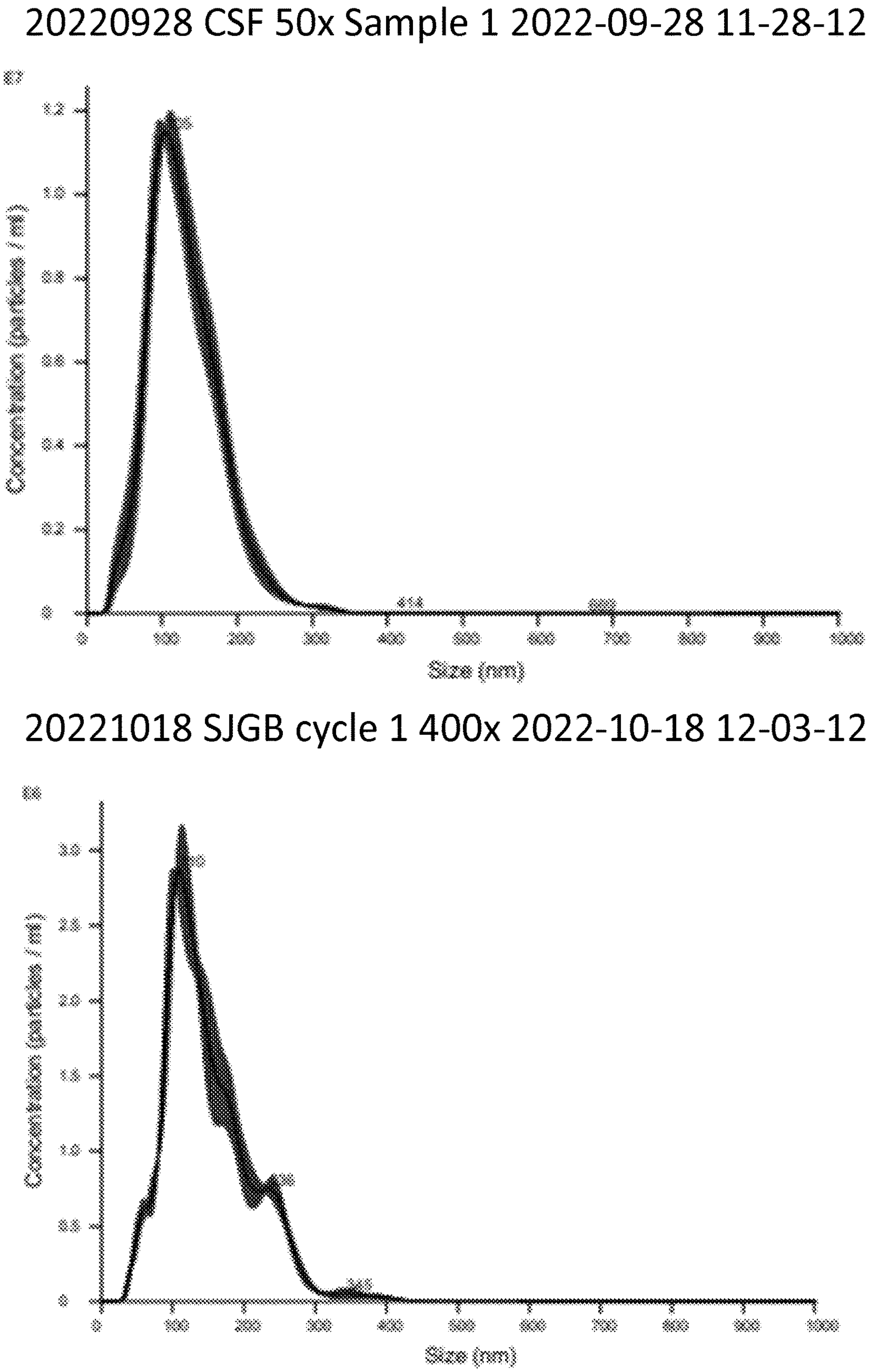
FIGS. 11A-11B: Nanosight profiles for CSF, MSCs, GBM cell line SJ-GBM2, and normal human astrocytes.
Figure 11B:
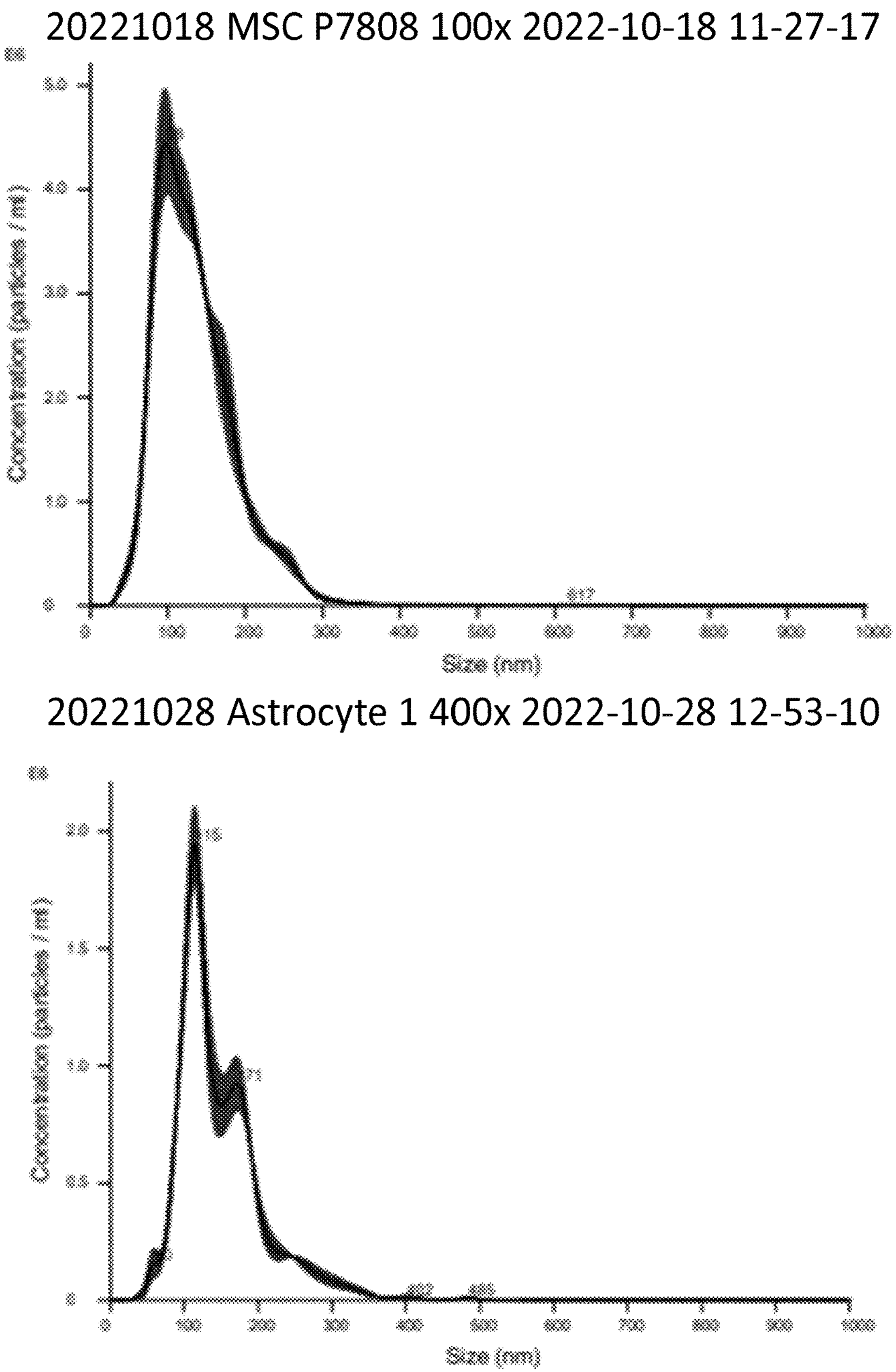
Figure 12A:
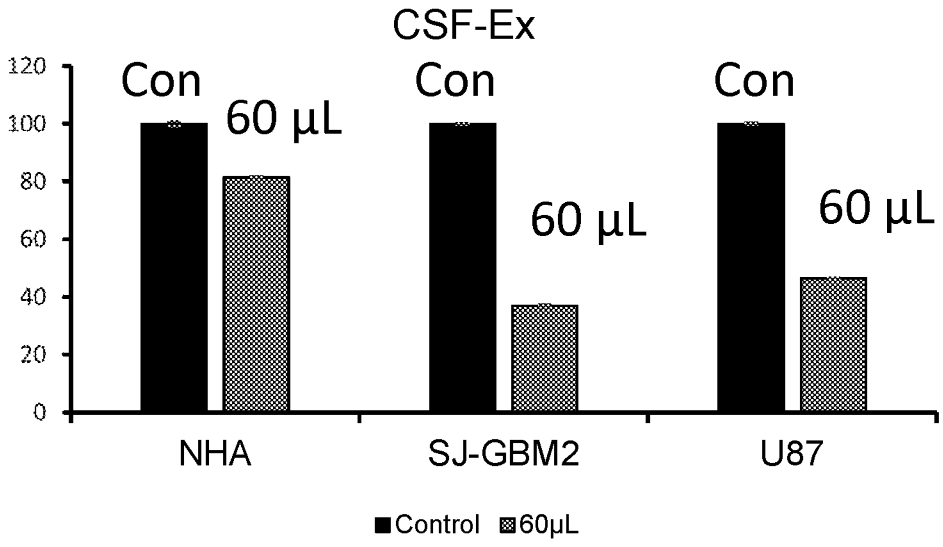
FIGS. 12A-12D: Cell viability of NHA, SJ-GBM2, and U87 after exposing with CAP modified extracellular vesicles for 24 hours. Exosomes were isolated by ultracentrifugation from patient derived cerebrospinal fluid, mesenchymal stromal cells (MSC-Ex), human normal astrocytes (Astrocytes-Ex), and human pediatric glioma cells (GBM-Ex)). Normal Human Astrocytes (NHA) and two Glioblastoma cell lines (SJ-GBM2 and U87) were used for this study. Cells were counted and approximately 10,000 cells were seeded in 96-well plates. After 24 hours incubation, cells were exposed to 60 μL of CAP modified exosomes with corresponding controls and incubated at 37° C. for 24 hours. After the incubation period, the viability of each cell line was estimated using Cell Counting Kit-8 (CCK-8). Briefly, 10 μL of CCK-8 reagent was added into each well, incubated for an hour and OD at 450 nm was measured using a microplate reader. The percentage of cell viability was calculated with their corresponding controls.
Figure 12B:
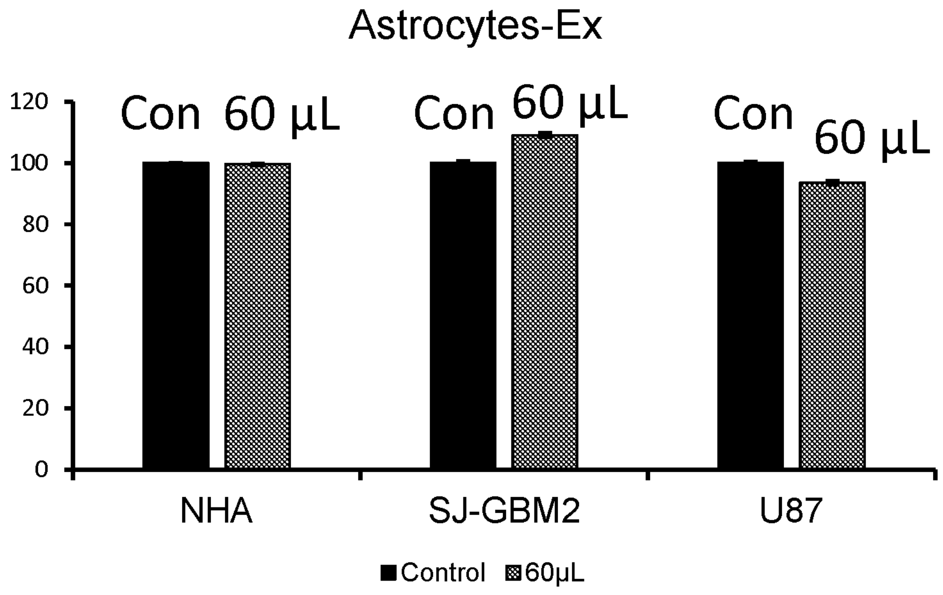
Figure 12C:
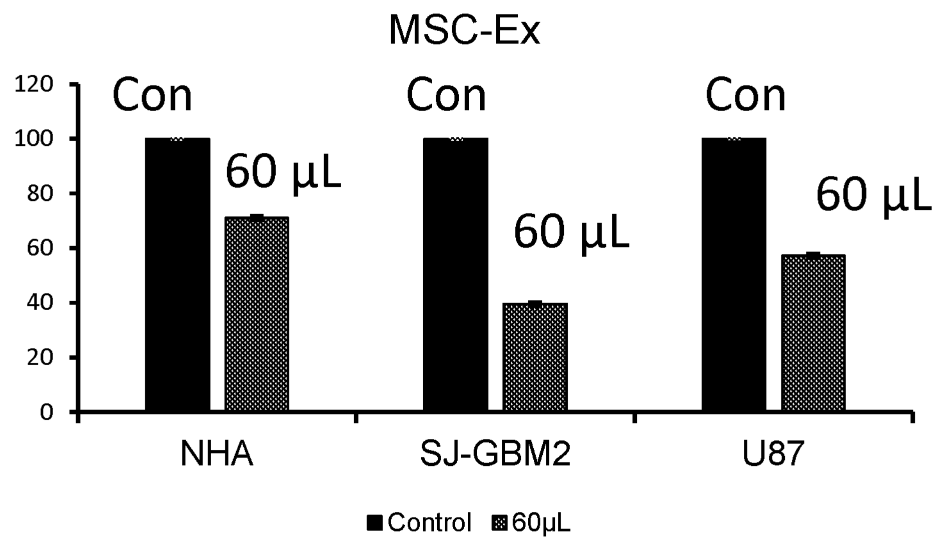
Figure 12D:
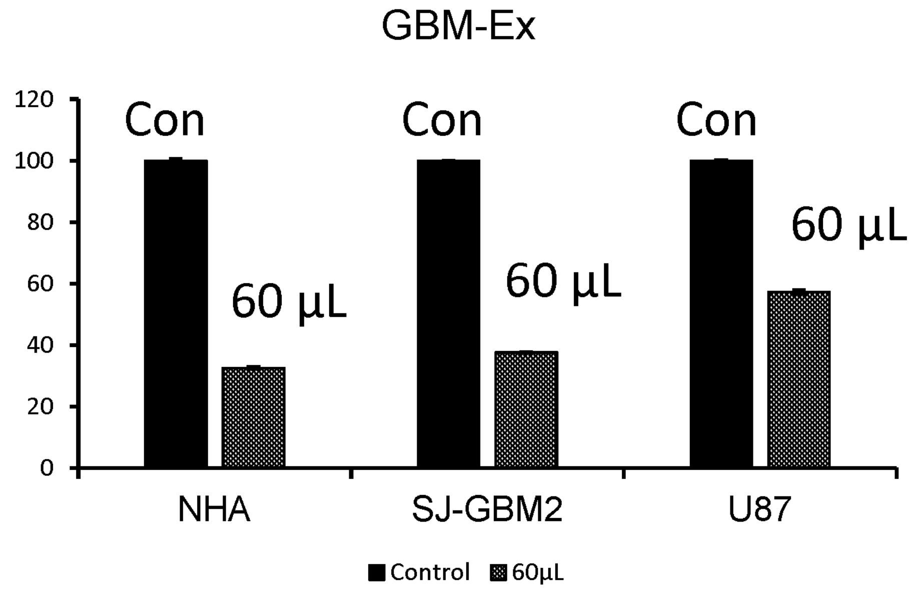

Materials and Methods:

Exosomes were isolated by ultracentrifugation from patient-derived CSF, bone marrow MSCs, NHA, and GBM cell line SJ-GBM2. NHAs and two Glioblastoma cell lines (SJ-GBM2 and U87) were used to test the effects of CAP-modified exosomes prepared according to the methodology of Example 1. Extracellular vesicles (EVs) were isolated directly from biological fluid (CSF) or from cell culture supernatants using a modified two-step centrifugation process as described by Thery C. et al. Curr Protoc Cell Biol (2006). For the isolation from cell culture supernatants, cells (bone marrow MSCs, NHA, and GBM cell line SJ-GBM2) were grown in their serum-containing standard culture media in culture flasks to confluency. The cells were then washed to remove culture media with PBS and media replaced with a serum-free media (StemPro MSC serum-free media (SFM) Gibco Life Technologies). The serum-containing standard culture media was replaced with SFM because serum contains endogenous EVs. After 18-24 hours of incubation at 37° C., 5% $CO_2$, the SFM cell supernatant containing the EVs and designated here as conditioned media (CM) was harvested. The CSF or CM from cells were centrifuged at a low-speed spin (2000×g at 4° C. for 20 minutes) to remove any cell debris and/or aggregates. The supernatant was then harvested and placed in 30 ml conical polypropylene ultracentrifuge tubes (Beckman Coulter Inc, Brea, CA, USA) and then centrifuged at 100,000 g avg at 4° C. for 2 hours using Optima™ L-80XP Ultracentrifuge (Beckman Coulter Inc,) in an SW-28 rotor (Beckman Coulter, Inc.). The supernatant was removed by aspiration, and tubes inverted to drain the excess fluid from the EV pellet. EVs were then re-suspended in PBS proportional to the starting volume at 100 μL of PBS per 30 mL of CSF or CM stored at −80° C. The EVs were quantified as number of particles/mL, and size range (nm) distribution determined using Nanoparticle Tracking Analysis (NTA) using a Nanosight NS300 instrument. The Nanosight profiles for CSF, MSCs, GBM cell line SJ-GBM2 and normal human astrocytes are shown in FIG. 11. The results indicate that the EVs isolated from the different sources showed similar size ranges consistent with exosomes. Importantly, all subsequent cytotoxicity experiments comparing EVs types treated with CAP used the equivalent numbers of EVs based on the NTA particle analysis.

Approximately 10,000 cells were seeded in 96-well plates. After 24 hours incubation, cells were exposed to 60 μL of CAP-modified exosomes with corresponding controls and incubated at 37° C. for 24 hours. After the incubation period, the viability of each cell line was estimated using Cell Counting Kit-8 (CCK-8). Briefly, 10 μL of CCK-8 reagent was added into each well, incubated for an hour, and OD at 450 nm was measured using a microplate reader. The percentage of cell viability was calculated with their corresponding controls.

Results:

The results are shown in FIGS. 12A-12D. CAP-modified exosomes isolated from CSF killed significantly more glioma cells (FIG. 12A), resulting in the viability of 36% and 46% in SJ-GBM2 and U87, respectively. At the same time, CAP-modified CSF-derived exosomes did not affect normal astrocytes significantly, as they were 81.3% alive after 24 hours. Treatment with CAP-modified MSC-derived exosomes (FIG. 12C) also resulted in a significant decline in the cell viability of both glioblastoma cells, while the astrocytes were unaffected by the treatment. On the other hand, the treatment with CAP-modified NHA-derived exosomes (FIG. 12B) did not kill any cells, cancerous or non-cancerous. Moreover, one of the cancer cells (SJ-GBM2) treated with NHA exosomes showed a slight cell proliferation at the end of incubation. Lastly, the CAP-modified GBM-derived exosomes (FIG. 12D) significantly killed both cancer lines as well as normal cells.

Conclusion:

CAP-modified exosomes isolated from CSF and MSC selectively kill glioma cells without harming normal astrocytes. These results indicate that such CAP-modified exosomes may be a useful way to treat GBM and perhaps other cancer types. Moreover, these results suggest that such treatments may not be harmful to non-cancerous tissues.

Example 3: Effect of CAP-Modified MSC-Derived Exosomes on Different Cancer Types Introduction:

This example determines the effects of CAP-modified MSC-derived exosomes on other cancer types.

Materials and Methods:

MSCs are expanded and their exosomes are isolated as described above. Approximately 10,000 cells from each cancer cell line (neuroblastoma, Wilms, breast cancer, colon cancer, lung cancer, and pancreatic cancer cells) and their homologous cell lines are seeded in 96-well plates. After 24 hours incubation, cells are exposed to 60 μL of CAP-modified MSC-derived exosomes with corresponding controls and incubated at 37° C. for 24 hours. After the incubation period, the viability of each cell line is determined using Cell Counting Kit-8 (CCK-8). The percentage of cell viability is calculated with their corresponding controls.

Results and Conclusion:

It is anticipated that CAP-modified exosomes isolated from MSCs selectively kill cancer cells without harming normal cells.

Example 4: Effect of CAP-Modified MSC-Derived Exosomes on Human Solid Tumors In Vivo Introduction:

This example determines the effects of CAP-modified MSC-derived exosomes on animal models of human solid cancers.

Materials and Methods:

MSCs are expanded and their exosomes are isolated as described above. Animal models of glioblastoma, neuroblastoma, and Wilms, breast, colon, lung, and pancreatic cancers are established. After solid cancer tumors reach an appropriate size, therapeutically effective doses of CAP-modified MSC-derived exosomes are administered to the tumor bearing animals and corresponding control animals (without tumors). After administration, tumor size, animal weight, and animal survival are monitored and measured over a period of time.

Results and Conclusion:

It is anticipated that CAP-modified exosomes isolated from MSCs selectively kill cancer cells without harming the animals.

REFERENCES

1. Stupp, R. et al. Effects of radiotherapy with concomitant and adjuvant temozolomide versus radiotherapy alone on survival in glioblastoma in a randomised phase III study: 5-year analysis of the EORTC-NCIC trial. The Lancet Oncology 10, 459-466 (2009).
2. Lu, V. M., Jue, T. R., McDonald, K. L. & Rovin, R. A. The Survival Effect of Repeat Surgery at Glioblastoma Recurrence and its Trend: A Systematic Review and Meta-Analysis. World Neurosurgery 115, 453-459.e3 (2018).
3. Raposo, G. & Stoorvogel, W. Extracellular vesicles: Exosomes, microvesicles, and friends. Journal of Cell Biology 200, 373-383 (2013).
4. Hessvik, N. P. & Llorente, A. Current knowledge on exosome biogenesis and release. Cellular and Molecular Life Sciences (2018) doi:10.1007/s00018-017-2595-9.
5. Bang, C. & Thum, T. Exosomes: New players in cell-cell communication. International Journal of Biochemistry and Cell Biology 44, 2060-2064 (2012).
6. Maia, J., Caja, S., Strano Moraes, M. C., Couto, N. & Costa-Silva, B. Exosome-based cell-cell communication in the tumor microenvironment. Frontiers in Cell and Developmental Biology 6, 1-19 (2018).
7. Kahroba, H., Hejazi, M. S. & Samadi, N. Exosomes: from carcinogenesis and metastasis to diagnosis and treatment of gastric cancer. Cellular and Molecular Life Sciences (2019) doi:10.1007/s00018-019-03035-2.
8. D'Asti, E. et al. Oncogenic extracellular vesicles in brain tumor progression. Frontiers in Physiology (2012) doi: 10.3389/fphys.2012.00294.

9. Melo, S. A. et al. Cancer Exosomes Perform Cell-Independent MicroRNA Biogenesis and Promote Tumorigenesis. Cancer Cell 26, 707-721 (2014).
10. Le, M. T. N. et al. MiR-200-containing extracellular vesicles promote breast cancer cell metastasis. Journal of Clinical Investigation 124, 5109-5128 (2014).
11. Ghaffari-Makhmalbaf, P. et al. Docosahexaenoic acid reverses the promoting effects of breast tumor cell-derived exosomes on endothelial cell migration and angiogenesis. Life Sciences 264, 118719 (2020).
12. Aslan, C. et al. Docosahexaenoic acid (DHA) inhibits pro-angiogenic effects of breast cancer cells via down-regulating cellular and exosomal expression of angiogenic genes and microRNAs. Life Sciences 258, 118094 (2020).
13. Welz, C. et al. Cold atmospheric plasma: A promising complementary therapy for squamous head and neck cancer. PLOS ONE 10, 1-15 (2015).
14. Yan, D., Sherman, J. H. & Keidar, M. Cold atmospheric plasma, a novel promising anti-cancer treatment modality. Oncotarget 8, 15977-15995 (2016).
15. Reuter, S. et al. From RONS to ROS: Tailoring plasma jet treatment of skin cells. IEEE Transactions on Plasma Science (2012) doi:10.1109/TPS.2012.2207130.
16. Cheng, X. et al. The effect of tuning cold plasma composition on glioblastoma cell viability. PLOS ONE 9, 1-9 (2014).

What is claimed is:

1. A method for generating CAP-modified extracellular vesicles (EVs) for the treatment of cancer, the method comprising the steps of:

(a) obtaining a sample of cancer cells or tissues of cancer cell origin;
(b) isolating EVs from the sample;
(c) preparing a cold atmospheric plasma (CAP); and
(d) exposing the EVs to the CAP to modify the EVs with CAP-derived reactive oxygen and nitrogen species.

2. The method of claim 1, wherein the EVs comprise exosomes (30-200 nm), microvesicles (50-1000 nm), and/or apoptotic bodies (500-2000 nm).

3. The method of claim 1, wherein the sample is a biopsy, a fluid, a perfusate of an organ, media collected from a homogenate of an organ, a cultured cell, a cultured tissue, or a cultured organ.

4. The method of claim 1, wherein the modified EVs comprise long half-life reactive oxygen and nitrogen species (RONS).

5. The method of claim 1, wherein the cancer cell is derived from glioblastoma, neuroblastoma, Wilms' tumor, breast cancer, colorectal cancer, lung cancer, liver cancer, kidney cancer, appendiceal cancer, desmoplastic small cell cancer, mesothelioma, ovarian cancer, peritoneal cancer, gastric cancer, malignant ascites, bladder cancer, blood cancer, bone cancer, soft tissue cancer, skin cancer, or pancreatic cancer.

6. The method of claim 1, wherein the tissue of cancer cell origin comprises central nervous system (CNS)-associated tissue, skin tissue, liver tissue, bone tissue, soft tissue, kidney tissue, breast tissue, colonic tissue, pleural fluid, peritoneal fluid, urine, serum, lung tissue, or pancreatic tissue.

7. The method of claim 6, wherein the central nervous system (CNS)-associated tissue comprises cerebrospinal fluid.

8. The method of claim 1, wherein the tissue of cancer cell origin is allogeneic, xenogeneic, or obtained from an individual to be treated.

9. The method of claim 1, wherein the tissue of cancer cell origin is differentiated from an embryonic or induced pluripotent stem cell.

10. The method of claim 1, wherein the EVs are isolated from the sample by ultracentrifugation, ultrafiltration, size exclusion chromatography, precipitation, immunoaffinity capture, and/or a microfluidics-based isolation.

11. The method of claim 1, wherein the CAP is prepared from helium, argon, nitrogen, heliox, water vapor, and/or air or other gases.

12. The method of claim 11, wherein the CAP is prepared from helium.

13. The method of claim 1, wherein the EVs are exposed to the CAP for about 1 minute to about 30 minutes.

14. A method for generating CAP-modified EVs for the treatment of a cancer, the method comprising the steps of:

(a) differentiating a cell or a tissue from an embryonic or induced pluripotent stem cell, wherein the cell or tissue is differentiated into a cell or tissue of cancer origin;
(b) isolating EVs from the differentiated cell or tissue;
(c) preparing a cold atmospheric plasma (CAP); and
(d) exposing the EVs to the CAP to modify the EVs with CAP-derived reactive oxygen and nitrogen species.

15. The method of claim 14, wherein the cell is a mesenchymal stromal cell, an astrocyte, a monocyte, a macrophage, a dendritic cell, a T cell, a B-cell, a fibroblast, or a stem cell.

16. A method of treating cancer in a subject in need thereof, comprising:

(a) obtaining a sample from a cancerous tumor or a tissue of cancerous tumor origin;
(b) isolating EVs from the sample;
(c) preparing a cold atmospheric plasma (CAP);
(d) exposing the EVs to the CAP to modify the EVs with CAP-derived reactive oxygen and nitrogen species; and
(e) administering a therapeutically effective amount of the CAP-modified EVs to the subject, wherein administration of the CAP-modified EVs kills tumor cells, suppresses tumor cell growth, and/or slows tumor cell growth.

17. The method of claim 16, wherein the therapeutically effective amount of CAP-modified EVs comprises about $1\times10^{11}$ to about $1\times10^{14}$ EVs.

18. The method of claim 17, wherein the therapeutically effective amount of CAP-modified EVs is administered to a subject in a dose of about $2\times10^{10}$/kg to about $1\times10^{14}$/kg.

* * * * *